US008609391B2

(12) United States Patent
Oh et al.

(10) Patent No.: US 8,609,391 B2
(45) Date of Patent: Dec. 17, 2013

(54) MANNOSE-6-PHOSPHATE ISOMERASE, MUTANT THEREOF, AND USE THEREOF

(75) Inventors: Deok Kun Oh, Seoul (KR); Soo Jin Yeom, Seoul (KR)

(73) Assignee: Konkuk University Industrial Cooperation Corp., Seoul (KR)

( * ) Notice: Subject to any disclaimer, the term of this patent is extended or adjusted under 35 U.S.C. 154(b) by 22 days.

(21) Appl. No.: 13/503,081

(22) PCT Filed: Oct. 22, 2010

(86) PCT No.: PCT/KR2010/007295

§ 371 (c)(1), (2), (4) Date: Apr. 20, 2012

(87) PCT Pub. No.: WO2011/049409

PCT Pub. Date: Apr. 28, 2011

(65) Prior Publication Data

US 2012/0270274 A1 Oct. 25, 2012

(30) Foreign Application Priority Data

Oct. 23, 2009 (KR) ........................ 10-2009-0101300
Jun. 29, 2010 (KR) ........................ 10-2010-0062366
Jul. 14, 2010 (KR) ........................ 10-2010-0067901

(51) Int. Cl.
*C12N 9/90* (2006.01)
*C12N 9/00* (2006.01)
*C07K 1/00* (2006.01)

(52) U.S. Cl.
USPC ............................ 435/233; 435/183; 530/350

(58) Field of Classification Search
None
See application file for complete search history.

(56) References Cited

PUBLICATIONS

NCBI GenBank Accession No. BAD71168, "putative mannose-6-phosphate isomerase [*Thermus thermophilus* HB8]" May 23, 2009.
Soo-Jin Yeom et al., "Molecular Characterization of a novel thermostable mannose-6-phosphate isomerase from *Thermus thermophilus*", Biochimie, 2011, 93, 1659-1667.
Soo-Jin Yeom et al., "Characterization of a mannose-6-phosphate isomerase from *Geobacillus thermodenitrificans* that converts monosaccharides", Biotechnology Letter. Apr. 24, 2009, vol. 31(8), pp. 1273-1278.
Soo-Jin Yeom et al., "Substrate specificity of a mannose-6-phosphate isomerase from *Bacillus subtilis* and its application in the production of L-ribose", Applied and Environmental Microbiology. May 15, 2009, vol. 75, pp. 4705-4710.
Soo-Jin Yeom et al., "Characterization of a mannose-6-phosphate isomerase from *Thermus thermophilus* and increased L-ribose production by its R142N mutant", Applied and Environmental Microbiology., Nov. 29, 2010, vol. 77,pp. 762-767.
Hui-Ju Lee et al., "Identification of amino acid residues important for the phosphomannose isomerase activity of Ps1B in *Pseudomonas aeruginosa* PAO1", FEBS Letters., 2008, vol. 582, No. 23, pp. 3479-3483.
NCBI GenBank Accession No. YP_001127480, "Mannnose-6 phosphate isomelase [*Geobacillus thermodenitrificans* NG80-2", Apr. 28, 2010.

*Primary Examiner* — Suzanne M Noakes
*Assistant Examiner* — Jae W Lee
(74) *Attorney, Agent, or Firm* — Lexyoume IP Meister, PLLC.

(57) ABSTRACT

New mannose-6-phasphate isomerase, mutant enzyme thereof, and a method of producing L-ribose using the enzyme are provided, and more specifically, mannose-6-phosphate isomerase, mutant enzyme thereof, recombinant expression vectors including relevant genes, microorganisms transformed with the vectors, a method of producing mannose-6-phosphate isomerase or mutant thereof in bulk using them, and a high yield method of producing L-ribose using the mannose-6-isomerase or the mutant thereof, are provided.

2 Claims, 14 Drawing Sheets

[illegible]
[illegible]
[illegible]
[illegible]
[illegible]
[illegible]
[illegible]
[illegible]
[illegible]
[illegible]

FIG. 9

ATGAGGCGGTTGGAGCCCAAACCCGTGGCGCGGATCTGGGGGGGAAGCGCCCTCGGCTTCGGCCCCGGGA
TCGGGGAGGTCTGGCTTGCCGAGGCCCCCCTGCTCGTGAAGCTCCTTGACCCCGCGGACTGGCTTTCCGT
CCAGGTCCACCCGCCCCCACGAGTACGCCCTCCGGGTGGAGGGCAAGCCGGGGAAGTACGAGGCCTGGTAC
GTCCTCTCCCCGGGGGAGCTGGTCTACGGCCTGGCCCGCCCCGTGAGCCCGGAGGAGCTTCGGGAAAGGG
CCTTGGCCGGGACCCTGGAGGAGGTGCTGCGCCGCGTCCGGGTGGAGCCCGGCCAGGTCCTCTACCTGCC
CGCGGGGACGATCCACGCCCTGGGCCCGGGGGTCCGGGTCTACGAGGTCCAGACCCCCTCGGACCTCACC
TACAATCTCTACGACTACGGCAGGCCGCGGGAGCTCCACCTGGAGAAGGCCCTGGACGTGGCCATCCTGG
AGCCCACCCCCCTCACCCTGCCCCCGCCCGAGCCGGTCTTGGGCGGGGAGAGGCTCCTTTCCACCCCCTT
CTTTGACCTTTTGCGGCTACCCCTTGGCGGGGAAGCTTTGGGTGCGGGCGGAGGCCCCACCCTCCTCACC
CTCCTCGAGGGGGAGGCCCGGCTTAAGGAGGAGGTCTTGCGGCCGCCCGCCACCCTCCTTTTGGAGCCCG
GGGAGGAGGCGGTCTTCCGGGGCGAGGGGCTCTGGCTTGCCGCCCTGGCCAAGGAGGGGGCGTGA

FIG. 10

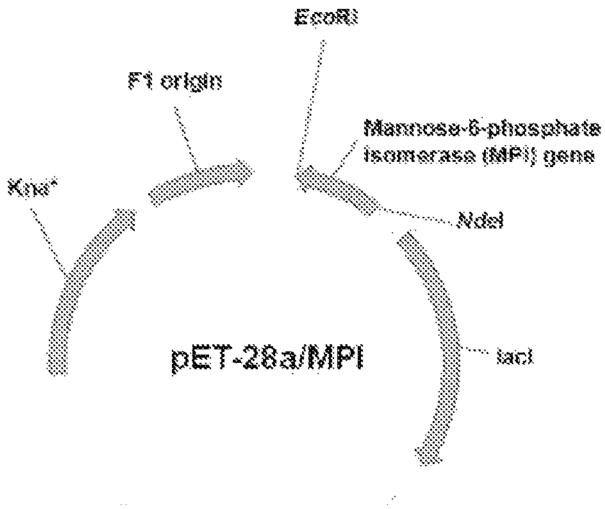

FIG. 17

ATGGACCTTGAACCGATTTTTCTCACTCCTGTCTTCCAAGAGCGCATTTGGGGCGGCACGAAGCTCGCCG
AACGGTTCGGCTACGATATCCCGTCATCGCAAACAGGGGAATGTTGGGCGGTATCGGCCCATCCGCACGG
ACAGACGGTTGTCGCCCCGCGGGCCGTTTCAAGGGATGACGCTTGGACAGCTATGGGAGGAGCGCCGCGAC
TTGTTCGGCAATTTTCCATCCGATCGCTTTCCGTTGCTGACGAAAATTTTAGACGCCAACGCCGATTTGT
CCGTCCAAGTCCATCCGGATGACGACTATGCAAAAACAAACGAAGGTGGGGAGCTCGGTAAGACAGAATG
TTGGTACATTATCGACTGCAAGCCGGGCGCCCAGTTAATTTACGGCCATTATGCCCAAACGAAAGAAGAG
CTGGCGCGCCATGATGGAGGCGGGAGAATGGGATCGTTTGCTGCGGAAAGTACCGATCCATCCCGGTGACT
TCTTCTATGTCCCGAGCGGCACGATTCACGCCCTCTGTGAGGGGACGCTTGTTCTCGAGACGCAGCAAAG
CTCTGACACGACTTATCGCGTCTACGATTACGACCGCGTCGACAGCCAAGGCGGAAGCGTGAGCTCCAC
TTAGAGAAAGCCATTGACGTCACCACTGTCCCGCATCGCGACACCGATGTCCAGCCCCATGTCGCCAACA
TGCCTGGCGCAACCGTGACGACCTTTGTGGAGGGTGACTACTTTGGCGTCCAAAAATGGCATGTCCATGG
AGAAGCCGAGTGGGAGCAGACGAAGCCATTTCTCATCGTCAGCATCCTTCAAGGAGAGGGCGAGCTTGTT
CACGGCGAGCGTACATACCCGATCCGCCAAGGTGACCATTTTATTTTGCCGCACCAATTCGGCCGGTTTG
CGATTCGTGGCACACTTGAAGCCATTGCCTCTTGGCCACGGAAAGGCAAATAA

FIG. 18

ATGGACCTTGAACCGATTTTTCTCACTCCTGTCTTCCAAGAGCGCATTTGGGGCGGCACGGAGCTCGCCG
AACGGTTCGGCTACGATATCCCGTCATCGCAAACAGGGGAATGTTGGGCGGTATCGGCCCATCCGCACGG
ACAGACGGTTGTCGCCCCGCGGGCCGTTTCAAGGGATGACGCTTGGACAGCTATGGGAGGAGCGCCGCGAC
TTGTTCGGCACTTTTCCATCCGATCGCTTTCCGTTGCTGACGAAAATTTTAGACGCCAACGCCGATTTGT
CCGTCCAAGTCCATCCGGATGACGACTATGCAAAAACAAACGAAGGTGGGGAGCTCGGTAAGACAGAATG
TTGGTACATTATCGACTGCAAGCCGGGCGCCCAGTTAATTTACGGCCATTATGCCCAAACGAAAGAAGAG
CTGGCGCGCCATGATGGAGGCGGGAGAATGGGATCGTTTGCTGCGGAAAGTACCGATCCATCCCGGTGACT
TCTTCTATGTCCCGAGCGGCACGATTCACGCCCTCTGTGAGGGGACGCTTGTTCTCGAGACGCAGCAAAG
CTCTGACACGACTTATCGCGTCTACGATTACGACCGCGTCGACAGCCAAGGCGGAAGCGTGAGCTCCAC
TTAGAGAAAGCCATTGACGTCACCACTGTCCCGCATCGCGACACCGATGTCCAGCCCCATGTCGCCAACA
GGCCTGGCGCAACCGTGACGACCTTTGTGGAGGGTGACTACTTTGGCGTCCAAAAATGGCATGTCCATGG
AGAAGCCGAGTGGGAGCAGACGAAGCCATTTCTCATCGTCAGCATCCTTCAAGGAGAGGGCGAGCTTGTT
CACGGCGAGCGTACATACCCGATCCGCCAAGGTGACCATTTTATTTTGCCGCACCAATTCGGCCGGTTTG
CGATTCGTGGCACACTTGAAGCCATTGCCTCTTGGCCACGGAAAGGCAAATAA

FIG. 19

ATGGACCTTGAACCGATTTTTCTCACTCCTGTCTTCCAAGAGCGCATTTGGGGCGGCACGAAGCTCGCCG
AACGGTTCGGCTACGATATCCCGTCATCGCAAACAGGGGAATGTTGGGCGGTATCGGCCCATCCGCACGG
ACAGACGGTTGTCGCCCGCGGGCCGTTTCAAGGGATGACGCTTGGACAGCTATGGGAGGGCGCCCGCGAC
TTGTTCGGCAATTTTTCCATCCGATCGCTTTCCGTTGCTGACGAAAATTTTAGACGCCAACGCCGATTTGT
CCGTCCAAGTCCATCCGGATGACGACTATGCAAAAACAAACGAAGGTGGGGAGCTCGGTAAGACAGAATG
TTGGTACATTATCGACTGCAAGCCGGGCGCCCAGTTAATTTACGGCCATTATGCCCAAACGTAAGAAGAG
CTGCGCGCCATGATGGAGGCGGGAGAATGGGATCGTTTGCTGCGGAAAGTACCGATCCATCCCGGTGACT
TCTTCTATGTCCCGAGCGGCACGATTCACGCCCTCTGTGAGGGGACGCTTGTTCTCGAGACGCAGCAAAG
CTCTGACACGACTTATCGCGTCTACGATTACGACCGCGTCGACAGCCAAGGGCGGAAGCGTGAGCTCCAC
TTAGAGAAAGCCATCGACGTCACCACTGTCCCGCATCGCGACACCGATGTCCAGCCCCATGTCGCCAACA
TGCCTGGCGCAATCGTGACGACCTTTGTGGAGGGTGACTACTTTGGCGTCCAAAAATGGCATGTCCATGG
AGAAGCCGAGTGGGAGCAGACGAAGCCATTTCTCATCGTCAGCATCCTTCAAGGAGAGGGCGAGCTTGTT
CACGGCGAGCGTACATACCCGATCCGCCAAGGTGACCATTTTATTTTGCCGCACCAATTCGGCCGGTTTG
CGATTCGTGGCACACTTGAAGCCATTGCCTCTTGGCCACGGAAAGGCAAATAA

FIG. 20

ATGGACCTTGAACCGATTTTTCTCACTCCTGTCTTCCAAGAGCGCATTTGGGGCGGCACGAAGCTCGCCG
AACGGTTCGGCTACGATATCCCGTCATCGCAAACAGGGGAATGTTGGGCGGTATCGGCCCATCCGCACGG
ACAGACGGTTGTCGCCCGCGGGCCGTTTCAAGGGATGACGCTTGGACAGCTATGGGAGGAGCGCCGCGAC
TTGTTCGGCAATTTTTCCATCCGATCGCTTTCCGTTGCTGACGAAAATTTTAGACGCCAACGCCGATTTGT
CCGTCCAAGTCCATCCGGATGACGACTATGCAAAAACAAACGAAGGTGGGGAGCTCGGTAAGACAGAATG
TTGGTACATTATCGACTGAAGGCCGGGCGCCCAGTTTATTTACGGCCATTATGCCCAAACGAAAGAAGAG
CTGCGCGCCATGATGGAGGCGGGAGAATGGGATCGTTTGCTGCGGAAAGTACCGATCCATCCCGGTGACT
TCTTCTATGTCCCGAGCGGCACGATTCACGCCCTCTGTGAGGGGACGCTTGTTCTCGAGACGCAGCAAAG
CTCTGACACGACTTATCGCGTCTACGATTACGACCGCCGTCGACAGCCAAGGGCGGAAGCGTGAGCTCCAC
TTAGAGAAAGCCATTGACGTCACCACTGTCCCGCATCGCGACACCGATGTCCAGCCCCATGTCGCCAACA
TGCCTGGCGCAACCGTGACGAGCTTTGTGGAGGGTGACTACTTTGGCGTCCAAAAATGGCATGTCCATGG
AGAAGCCGAGTGGGAGCAGACGAAGCCATTTCTCATCGTCAGCATCCTTCAAGGAGAGGGCGAGCTTGTT
CACGGCGAGCGTACATACCCGATCCGCCAAGGTGACCATTTTATTTTGCCGCACCAATTCGGCCGGTTTG
CGATTCGTGGCACACTTGAAGCCATTGCCTCTTGGCCACGGAAAGGCAAATAA

FIG. 21

ATGGACCTTGAACCGATTTTTCTCACTCCTGTCTTCCAAGAGCGCATTTGGGGCGGCACGAAGCTCGCCG
AACGGTTCGGCTACGATATCCCGTCATCGCAAACAGGGGAATGTTGGGCGGTATCGGCCCATCCGCACGG
ACAGACGGTTGTCGCCCGCGGGCCGTTTCAAGGGATGACGCTTGGACAGCTATGGGAGGAGCGCCGCGAC
TTGTTCGGCAATTTTTCCATCCGATCGCTTTCCGTTGCTGACGAAAATTTTAGACGCCAACGCCGATTTGT
CCGTCCAAGTCCATCCGGATGACGACTATGCAAAAACAAACGAAGGTGGGGAGCTCGGTAAGACAGAATG
TTGGTACATTATCGACTGAAGGCCGGGCGCCCAGTTTATTTACGGCCATTATGCCCAAACGAAAGAAGAG
CTGCGCGCCATGATGGAGGCGGGAGAATGGGATCGTTTGCTGCGGAAAGTACCGATCCATCCCGGTGACT
TCTTCTATGTCCCGAGCGGCACGATTCACGCCCTCTGTGAGGGGACGCTTGTTCTCGAGACGCAGCAAAG
CTCTGACACGACTTATCGCGTCTACGATTACGACCGCCGTCGACAGCCAAGGGCGGAAGCGTGAGCTCCAC
TTAGAGAAAGCCATTGACGTCACCACTGTCCCGCATCGCGACACCGATGTCCAGCCCCATGTCGCCAACA
TGCCTGGCGCAACCGTGACGAGCTTTGTGGAGGGTGACTACTTTGGCGTCCAAAAATGGCATGTCCATGG
AGAAGCCGAGTGGGAGCAGACGAAGCCATTTCTCATCGTCAGCATCCTTCAAGGAGAGGGCGAGCTTGTT
CACGGCGAGCGTACATACCCGATCCGCCAAGGTGACCATTTTATTTTGCCGCACCAATTCGGCCGGTTTG
CGATTCGTGGCACACTTGAAGCCATTGCCTCTTGGCCACGGAAAGGCAAATAA

SEQUENCE LISTING

```
<160> NUMBER OF SEQ ID NOS: 16

<210> SEQ ID NO 1
<211> LENGTH: 255
<212> TYPE: PRT
<213> ORGANISM: Thermus thermophilus

<400> SEQUENCE: 1

Met Arg Arg Leu Glu Pro Lys Pro Val Ala Arg Ile Trp Gly Gly Ser
1               5                   10                  15

Gly Leu Gly Phe Gly Pro Gly Ile Gly Glu Val Trp Leu Ala Glu Ala
            20                  25                  30

Pro Leu Leu Val Lys Leu Leu Asp Pro Ala Asp Trp Leu Ser Val Gln
        35                  40                  45

Val His Pro Pro His Glu Tyr Ala Leu Arg Val Glu Gly Lys Pro Gly
    50                  55                  60

Lys Tyr Glu Ala Trp Tyr Val Leu Ser Pro Gly Glu Leu Val Tyr Gly
65                  70                  75                  80

Leu Ala Arg Pro Val Ser Arg Glu Glu Leu Arg Glu Arg Ala Leu Ala
                85                  90                  95

Gly Thr Leu Glu Glu Val Leu Arg Arg Val Arg Val Glu Pro Gly Gln
            100                 105                 110

Val Leu Tyr Leu Pro Ala Gly Thr Ile His Ala Leu Gly Pro Gly Val
        115                 120                 125

Arg Val Tyr Glu Val Gln Thr Pro Ser Asp Leu Thr Tyr Arg Leu Tyr
    130                 135                 140

Asp Tyr Gly Arg Pro Arg Glu Leu His Leu Glu Lys Ala Leu Asp Val
145                 150                 155                 160

Ala Ile Leu Glu Pro Thr Pro Leu Thr Leu Pro Pro Pro Glu Pro Val
                165                 170                 175
```

-continued

```
Leu Gly Gly Glu Arg Leu Leu Ser Thr Pro Phe Phe Asp Leu Leu Arg
            180                 185                 190

Tyr Pro Leu Ala Gly Lys Leu Trp Val Arg Ala Glu Gly Pro Thr Leu
        195                 200                 205

Leu Thr Leu Leu Glu Gly Glu Ala Arg Leu Lys Glu Glu Val Leu Arg
    210                 215                 220

Pro Pro Ala Thr Leu Leu Leu Glu Pro Gly Glu Glu Ala Val Phe Arg
225                 230                 235                 240

Gly Glu Gly Leu Trp Leu Ala Ala Leu Ala Lys Glu Gly Ala Glx
                245                 250                 255


<210> SEQ ID NO 2
<211> LENGTH: 321
<212> TYPE: PRT
<213> ORGANISM: Geobacillus thermodenitrificans

<400> SEQUENCE: 2

Met Asp Leu Glu Pro Ile Phe Leu Thr Pro Val Phe Gln Glu Arg Ile
  1               5                  10                  15

Trp Gly Gly Thr Lys Leu Ala Glu Arg Phe Gly Tyr Asp Ile Pro Ser
             20                  25                  30

Ser Gln Thr Gly Glu Cys Trp Ala Val Ser Ala His Pro His Gly Gln
         35                  40                  45

Thr Val Val Ala Arg Gly Pro Phe Gln Gly Met Thr Leu Gly Gln Leu
     50                  55                  60

Trp Glu Glu Arg Arg Asp Leu Phe Gly Asn Phe Pro Ser Asp Arg Phe
 65                  70                  75                  80

Pro Leu Leu Thr Lys Ile Leu Asp Ala Asn Ala Asp Leu Ser Val Gln
                 85                  90                  95

Val His Pro Asp Asp Asp Tyr Ala Lys Thr Asn Glu Gly Gly Glu Leu
            100                 105                 110

Gly Lys Thr Glu Cys Trp Tyr Ile Ile Asp Cys Lys Pro Gly Ala Gln
        115                 120                 125

Leu Ile Tyr Gly His Tyr Ala Gln Thr Lys Glu Glu Leu Arg Ala Met
    130                 135                 140

Met Glu Ala Gly Glu Trp Asp Arg Leu Leu Arg Lys Val Pro Ile His
145                 150                 155                 160

Pro Gly Asp Phe Phe Tyr Val Pro Ser Gly Thr Ile His Ala Leu Cys
                165                 170                 175

Glu Gly Thr Leu Val Leu Glu Thr Gln Gln Ser Ser Asp Thr Thr Tyr
            180                 185                 190

Arg Val Tyr Asp Tyr Asp Arg Val Asp Ser Gln Gly Arg Lys Arg Glu
        195                 200                 205

Leu His Leu Glu Lys Ala Ile Asp Val Thr Thr Val Pro His Arg Asp
    210                 215                 220

Thr Asp Val Gln Pro His Val Ala Asn Met Pro Gly Ala Thr Val Thr
225                 230                 235                 240

Thr Phe Val Glu Gly Asp Tyr Phe Gly Val Gln Lys Trp His Val His
                245                 250                 255

Gly Glu Ala Glu Trp Glu Gln Thr Lys Pro Phe Leu Ile Val Ser Ile
            260                 265                 270

Leu Gln Gly Glu Gly Glu Leu Val His Gly Glu Arg Thr Tyr Pro Ile
        275                 280                 285

Arg Gln Gly Asp His Phe Ile Leu Pro His Gln Phe Gly Arg Phe Ala
    290                 295                 300
```

-continued

Ile Arg Gly Thr Leu Glu Ala Ile Ala Ser Trp Pro Arg Lys Gly Lys
305 310 315 320

Glx

<210> SEQ ID NO 3
<211> LENGTH: 765
<212> TYPE: DNA
<213> ORGANISM: Thermus thermophilus

<400> SEQUENCE: 3
atgaggcggt tggagcccaa acccgtggcg cggatctggg ggggaagcgg cctcggcttc 60
ggccccggga tcggggaggt ctggcttgcc gaggcccccc tgctcgtgaa gctccttgac 120
cccgcggact ggctttccgt ccaggtccac ccgccccacg agtacgccct ccgggtggag 180
gggaagccgg ggaagtacga ggcctggtac gtcctctccc cgggggagct ggtctacggc 240
ctggcccgcc ccgtgagccg ggaggagctt cgggaaaggg ccttggccgg gaccctggag 300
gaggtgctgc gccgcgtccg ggtggagccg ggccaggtcc tctacctgcc cgcggggacg 360
atccacgccc tgggcccggg ggtccgggtc tacgaggtcc agaccccctc ggacctcacc 420
taccgcctct acgactacgg caggccgcgg gagctccacc tggagaaggc cctggacgtg 480
gccatcctgg agcccacccc cctcaccctg cccccgcccg agccggtctt gggcggggag 540
aggctccttt ccaccccctt ctttgacctt ttgcgctacc ccttggcggg gaagctttgg 600
gtgcgggcgg agggccccac cctcctcacc ctcctcgagg gggaggcccg gcttaaggag 660
gaggtcttgc ggccgcccgc caccctcctt ttggagcccg gggaggaggc ggtcttccgg 720
ggcgaggggc tctggcttgc cgccctggcc aaggaggggg cgtga 765

<210> SEQ ID NO 4
<211> LENGTH: 963
<212> TYPE: DNA
<213> ORGANISM: Geobacillus thermodenitrificans

<400> SEQUENCE: 4
atggaccttg aaccgatttt tctcactcct gtcttccaag agcgcatttg gggcggcacg 60
aagctcgccg aacggttcgg ctacgatatc ccgtcatcgc aaacagggga atgttgggcg 120
gtatcggccc atccgcacgg acagacggtt gtcgcccgcg ggccgtttca agggatgacg 180
cttggacagc tatgggagga gcgccgcgac ttgttcggca attttccatc cgatcgcttt 240
ccgttgctga cgaaaatttt agacgccaac gccgatttgt ccgtccaagt ccatccggat 300
gacgactatg caaaaacaaa cgaaggtggg gagctcggta agacagaatg ttggtacatt 360
atcgactgca agccgggcgc ccagttaatt tacggccatt atgcccaaac gaaagaagag 420
ctgcgcgcca tgatggaggc gggagaatgg gatcgtttgc tgcggaaagt accgatccat 480
cccggtgact tcttctatgt cccgagcggc acgattcacg ccctctgtga ggggacgctt 540
gttctcgaga cgcagcaaag ctctgacacg acttatcgcg tctacgatta cgaccgcgtc 600
gacagccaag ggcggaagcg tgagctccac ttagagaaag ccattgacgt caccactgtc 660
ccgcatcgcg acaccgatgt ccagccccat gtcgccaaca tgcctggcgc aaccgtgacg 720
acctttgtgg agggtgacta ctttggcgtc caaaaatggc atgtccatgg agaagccgag 780
tgggagcaga cgaagccatt tctcatcgtc agcatccttc aaggagaggg cgagcttgtt 840
cacggcgagc gtacataccc gatccgccaa ggtgaccatt ttattttgcc gcaccaattc 900
ggccggtttg cgattcgtgg cacacttgaa gccattgcct cttggccacg gaaaggcaaa 960

-continued

```
taa                                                                963

<210> SEQ ID NO 5
<211> LENGTH: 765
<212> TYPE: DNA
<213> ORGANISM: Artificial Sequence
<220> FEATURE:
<223> OTHER INFORMATION: synthesized from Thermus thermophilus

<400> SEQUENCE: 5

atgaggcggt tggagcccaa acccgtggcg cggatctggg ggggaagcgg cctcggcttc     60

ggccccggga tcggggaggt ctggcttgcc gaggcccccc tgctcgtgaa gctccttgac    120

cccgcggact ggctttccgt ccaggtccac ccgccccacg agtacgccct ccgggtggag    180

gggaagccgg ggaagtacga ggcctggtac gtcctctccc cgggggagct ggtctacggc    240

ctggcccgcc ccgtgagccg ggaggagctt cgggaaaggg ccttggccgg gaccctggag    300

gaggtgctgc gccgcgtccg ggtggagccg ggccaggtcc tctacctgcc cgcggggacg    360

atccacgccc tgggcccggg ggtccgggtc tacgaggtcc agaccccctc ggacctcacc    420

tacaatctct acgactacgg caggccgcgg gagctccacc tggagaaggc cctggacgtg    480

gccatcctgg agcccacccc cctcaccctg cccccgcccg agccggtctt gggcggggag    540

aggctccttt ccaccccctt ctttgacctt ttgcgctacc ccttggcggg gaagctttgg    600

gtgcgggcgg agggccccac cctcctcacc ctcctcgagg gggaggcccg gcttaaggag    660

gaggtcttgc ggccgcccgc caccctcctt ttggagcccg gggaggaggc ggtcttccgg    720

ggcgaggggc tctggcttgc cgccctggcc aaggaggggg cgtga                    765

<210> SEQ ID NO 6
<211> LENGTH: 963
<212> TYPE: DNA
<213> ORGANISM: Artificial Sequence
<220> FEATURE:
<223> OTHER INFORMATION: synthesized from Geobacillus
      thermodenitrificans

<400> SEQUENCE: 6

atggaccttg aaccgatttt tctcactcct gtcttccaag agcgcatttg gggcggcacg     60

gagctcgccg aacggttcgg ctacgatatc ccgtcatcgc aaacagggga atgttgggcg    120

gtatcggccc atccgcacgg acagacggtt gtcgcccgcg ggccgtttca agggatgacg    180

cttggacagc tatgggagga gcgccgcgac ttgttcggca cttttccatc cgatcgcttt    240

ccgttgctga cgaaaatttt agacgccaac gccgatttgt ccgtccaagt ccatccggat    300

gacgactatg caaaaacaaa cgaaggtggg gagctcggta agacagaatg ttggtacatt    360

atcgactgca agccgggcgc ccagttaatt tacggccatt atgcccaaac gaaagaagag    420

ctgcgcgcca tgatggaggc gggagaatgg gatcgtttgc tgcggaaagt accgatccat    480

cccggtgact tcttctatgt cccgagcggc acgattcacg ccctctgtga ggggacgctt    540

gttctcgaga cgcagcaaag ctctgacacg acttatcgcg tctacgatta cgaccgcgtc    600

gacagccaag ggcggaagcg tgagctccac ttagagaaag ccattgacgt caccactgtc    660

ccgcatcgcg acaccgatgt ccagccccat gtcgccaaca ggcctggcgc aaccgtgacg    720

acctttgtgg agggtgacta ctttggcgtc caaaaatggc atgtccatgg agaagccgag    780

tgggagcaga cgaagccatt tctcatcgtc agcatccttc aaggagaggg cgagcttgtt    840

cacggcgagc gtacataccc gatccgccaa ggtgaccatt ttattttgcc gcaccaattc    900

ggccggtttg cgattcgtgg cacacttgaa gccattgcct cttggccacg gaaaggcaaa    960
```

taa 963

<210> SEQ ID NO 7
<211> LENGTH: 963
<212> TYPE: DNA
<213> ORGANISM: Artificial Sequence
<220> FEATURE:
<223> OTHER INFORMATION: synthesized from Geobacillus thermodenitrificans

<400> SEQUENCE: 7
atggaccttg aaccgatttt tctcactcct gtcttccaag agcgcatttg gggcggcacg 60
aagctcgccg aacggttcgg ctacgatatc ccgtcatcgc aaacagggga atgttgggcg 120
gtatcggccc atccgcacgg acagacggtt gtcgcccgcg ggccgtttca agggatgacg 180
cttggacagc tatgggaggg gcgccgcgac ttgttcggca attttccatc cgatcgcttt 240
ccgttgctga cgaaaatttt agacgccaac gccgatttgt ccgtccaagt ccatccggat 300
gacgactatg caaaaacaaa cgaaggtggg gagctcggta agacagaatg ttggtacatt 360
atcgactgca agccgggcgc ccagttaatt tacggccatt atgcccaaac gtaagaagag 420
ctgcgcgcca tgatggaggc gggagaatgg gatcgtttgc tgcggaaagt accgatccat 480
cccggtgact tcttctatgt cccgagcggc acgattcacg ccctctgtga ggggacgctt 540
gttctcgaga cgcagcaaag ctctgacacg acttatcgcg tctacgatta cgaccgcgtc 600
gacagccaag ggcggaagcg tgagctccac ttagagaaag ccatcgacgt caccactgtc 660
ccgcatcgcg acaccgatgt ccagccccat gtcgccaaca tgcctggcgc aatcgtgacg 720
acctttgtgg agggtgacta ctttggcgtc caaaaatggc atgtccatgg agaagccgag 780
tgggagcaga cgaagccatt tctcatcgtc agcatccttc aaggagaggg cgagcttgtt 840
cacggcgagc gtacataccc gatccgccaa ggtgaccatt ttattttgcc gcaccaattc 900
ggccggtttg cgattcgtgg cacacttgaa gccattgcct cttggccacg gaaaggcaaa 960
taa 963

<210> SEQ ID NO 8
<211> LENGTH: 963
<212> TYPE: DNA
<213> ORGANISM: Artificial Sequence
<220> FEATURE:
<223> OTHER INFORMATION: synthesized from Geobacillus thermodenitrificans

<400> SEQUENCE: 8
atggaccttg aaccgatttt tctcactcct gtcttccaag agcgcatttg gggcggcacg 60
aagctcgccg aacggttcgg ctacgatatc ccgtcatcgc aaacagggga atgttgggcg 120
gtatcggccc atccgcacgg acagacggtt gtcgcccgcg ggccgtttca agggatgacg 180
cttggacagc tatgggagga gcgccgcgac ttgttcggca attttccatc cgatcgcttt 240
ccgttgctga cgaaaatttt agacgccaac gccgatttgt ccgtccaagt ccatccggat 300
gacgactatg caaaaacaaa cgaaggtggg gagctcggta agacagaatg ttggtacatt 360
atcgactgaa ggccgggcgc ccagtttatt tacggccatt atgcccaaac gaaagaagag 420
ctgcgcgcca tgatggaggc gggagaatgg gatcgtttgc tgcggaaagt accgatccat 480
cccggtgact tcttctatgt cccgagcggc acgattcacg ccctctgtga ggggacgctt 540
gttctcgaga cgcagcaaag ctctgacacg acttatcgcg tctacgatta cgaccgcgtc 600
gacagccaag ggcggaagcg tgagctccac ttagagaaag ccattgacgt caccactgtc 660
ccgcatcgcg acaccgatgt ccagccccat gtcgccaaca tgcctggcgc aaccgtgacg 720
acctttgtgg agggtgacta ctttggcgtc caaaaatggc atgtccatgg agaagccgag 780
tgggagcaga cgaagccatt tctcatcgtc agcatccttc aaggagaggg cgagcttgtt 840
cacggcgagc gtacataccc gatccgccaa ggtgaccatt ttattttgcc gcaccaattc 900
ggccggtttg cgattcgtgg cacacttgaa gccattgcct cttggccacg gaaaggcaaa 960
taa 963

<210> SEQ ID NO 9
<211> LENGTH: 963
<212> TYPE: DNA
<213> ORGANISM: Artificial Sequence
<220> FEATURE:
<223> OTHER INFORMATION: synthesized from Geobacillus thermodenitrificans

<400> SEQUENCE: 9
atggaccttg aaccgatttt tctcactcct gtcttccaag agcgcatttg gggcggcacg 60
aagctcgccg aacggttcgg ctacgatatc ccgtcatcgc aaacagggga atgttgggcg 120
gtatcggccc atccgcacgg acagacggtt gtcgcccgcg ggccgtttca agggatgacg 180
cttggacagc tatgggagga gcgccgcgac ttgttcggca attttccatc cgatcgcttt 240
ccgttgctga cgaaaatttt agacgccgac gccgatttgt ccgtccaagt ccatccggat 300
gacgactatg caaaaacaaa cgaaggtggg gagctcggta agacagaatg ttggtacatt 360
atcgactgca agccgggcgc ccagttaatt tacggccatt atgcccaaac gaaagaagag 420
ctgcgcgcca tgatggaggc gggagaatgg gatcgtttgc tgcggaaagt accgatccat 480
cccggtgact tcttctatgt cccgagcggc acgattcacg ccctctgtga ggggacgctt 540
gttctcgaga cgcagcaaag ctctgacacg acttatcgcg tctacgatta cgaccgcgtc 600
gacagccaag ggcggaagcg tgagctccac ttagagaaag ccattgacgt caccactgtc 660
ccgcatcgcg acaccgatgt ccagccccat gtcgccaaca tgcctggcgc aaccgtgacg 720
acctttgtgg agggtgacta ctttggcgtc caaaaatggc atgtccatgg agaagccgag 780
tgggagcaga cgaagccatt tctcatcgtc agcatccttc aaggagaggg cgagcttgtt 840
cacggcgagc gtacataccc gatccgccaa ggtgaccatt ttattttgcc gcaccaattc 900
ggccggtttg cgattcgtgg cacacttgaa gccattgcct cttggccacg gaaaggcaaa 960
taa 963

<210> SEQ ID NO 10
<211> LENGTH: 963
<212> TYPE: DNA
<213> ORGANISM: Artificial Sequence
<220> FEATURE:
<223> OTHER INFORMATION: synthesized from Geobacillus thermodenitrificans

<400> SEQUENCE: 10
atggaccttg aaccgatttt tctcactcct gtcttccaag agcgcatttg gggcggcacg 60
aagctcgccg aacggttcgg ctacgatatc ccgtcatcgc aaacagggga atgttgggcg 120
gtatcggccc atccgcacgg acagacggtt gtcgcccgcg ggccgtttca agggatgacg 180
cttggacagc tatgggagga gcgccgcgac ttgttcggca attttccatc cgatcgcttt 240
ccgttgctga cgaaaatttt agacgccgcc gccgatttgt ccgtccaagt ccatccggat 300
gacgactatg caaaaacaaa cgaaggtggg gagctcggta agacagaatg ttggtacatt 360

```
atcgactgca agccgggcgc ccagttaatt tacggccatt atgcccaaac gaaagaagag    420

ctgcgcgcca tgatggaggc gggagaatgg gatcgtttgc tgcggaaagt accgatccat    480

cccggtgact tcttctatgt cccgagcggc acgattcacg ccctctgtga ggggacgctt    540

gttctcgaga cgcagcaaag ctctgacacg acttatcgcg tctacgatta cgaccgcgtc    600

gacagccaag ggcggaagcg tgagctccac ttagagaaag ccattgacgt caccactgtc    660

ccgcatcgcg acaccgatgt ccagccccat gtcgccaaca tgcctggcgc aaccgtgacg    720

acctttgtgg agggtgacta ctttggcgtc caaaaatggc atgtccatgg agaagccgag    780

tgggagcaga cgaagccatt tctcatcgtc agcatccttc aaggagaggg cgagcttgtt    840

cacggcgagc gtacataccc gatccgccaa ggtgaccatt ttattttgcc gcaccaattc    900

ggccggtttg cgattcgtgg cacacttgaa gccattgcct cttggccacg gacaagcaaa    960

taa                                                                  963
```

```
<210> SEQ ID NO 11
<211> LENGTH: 963
<212> TYPE: DNA
<213> ORGANISM: Artificial Sequence
<220> FEATURE:
<223> OTHER INFORMATION: synthesized from Geobacillus
      thermodenitrificans

<400> SEQUENCE: 11

atggaccttg aaccgatttt tctcactcct gtcttccaag agcgcatttg gggcggcacg     60

aagctcgccg aacggttcgg ctacgatatc ccgtcatcgc aaacagggga atgttgggcg    120

gtatcggccc atccgcacgg acagacggtt gtcgcccgcg ggccgtttca agggatgacg    180

cttggacagc tatgggagga gcgccgcgac ttgttcggca attttccatc cgatcgcttt    240

ccgttgctga cgaaaatttt agacgccaac gccgatttgt ccgtccaagt ccatccggat    300

gacgactatg caaaaacaaa cgaaggtggg gagctcggta agacagaatg ttggtacatt    360

atcgactgca agccgggcgc ccagttcatt tacggccatt atgcccaaac gaaagaagag    420

ctgcgcgcca tgatggaggc gggagaatgg gatcgtttgc tgcggaaagt accgatccat    480

cccggtgact tcttctatgt cccgagcggc acgattcacg ccctctgtga ggggacgctt    540

gttctcgaga cgcagcaaag ctctgacacg acttatcgcg tctacgatta cgaccgcgtc    600

gacagccaag ggcggaagcg tgagctccac ttagagaaag ccattgacgt caccactgtc    660

ccgcatcgcg acaccgatgt ccagccccat gtcgccaaca tgcctggcgc aaccgtgacg    720

acctttgtgg agggtgacta ctttggcgtc caaaaatggc atgtccatgg agaagccgag    780

tgggagcaga cgaagccatt tctcatcgtc agcatccttc aaggagaggg cgagcttgtt    840

cacggcgagc gtacataccc gatccgccaa ggtgaccatt ttattttgcc gcaccaattc    900

ggccggtttg cgattcgtgg cacacttgaa gccattgcct cttggccacg gacaagcaaa    960

taa                                                                  963

<210> SEQ ID NO 12
<211> LENGTH: 963
<212> TYPE: DNA
<213> ORGANISM: Artificial Sequence
<220> FEATURE:
<223> OTHER INFORMATION: synthesized from Geobacillus
      thermodenitrificans
```

<400> SEQUENCE: 12
atggaccttg aaccgatttt tctcactcct gtcttccaag agcgcatttg gggcggcacg 60
aagctcgccg aacggttcgg ctacgatatc ccgtcatcgc aaacagggga atgttgggcg 120
gtatcggccc atccgcacgg acagacggtt gtcgcccgcg ggccgtttca agggatgacg 180
cttggacagc tatgggagga gcgccgcgac ttgttcggca attttccatc cgatcgcttt 240
ccgttgctga cgaaaatttt agacgccgcc gccgatttgt ccgtccaagt ccatccggat 300
gacgactatg caaaaacaaa cgaaggtggg gagctcggta agacagaatg ttggtacatt 360
atcgactgca agccgggcgc ccagttcatt tacggccatt atgcccaaac gaaagaagag 420
ctgcgcgcca tgatggaggc gggagaatgg gatcgtttgc tgcggaaagt accgatccat 480
cccggtgact tcttctatgt cccgagcggc acgattcacg ccctctgtga ggggacgctt 540
gttctcgaga cgcagcaaag ctctgacacg acttatcgcg tctacgatta cgaccgcgtc 600
gacagccaag ggcggaagcg tgagctccac ttagagaaag ccattgacgt caccactgtc 660
ccgcatcgcg acaccgatgt ccagccccat gtcgccaaca tgcctggcgc aaccgtgacg 720
acctttgtgg agggtgacta ctttggcgtc caaaaatggc atgtccatgg agaagccgag 780
tgggagcaga cgaagccatt tctcatcgtc agcatccttc aaggagaggg cgagcttgtt 840
cacggcgagc gtacataccc gatccgccaa ggtgaccatt ttattttgcc gcaccaattc 900
ggccggtttg cgattcgtgg cacacttgaa gccattgcct cttggccacg gacaagcaaa 960
taa 963

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
tttcatatga ggcggttgga gcccaa 26

<210> SEQ ID NO 14
<211> LENGTH: 26
<212> TYPE: DNA
<213> ORGANISM: Artificial Sequence
<220> FEATURE:
<223> OTHER INFORMATION: primer

<400> SEQUENCE: 14
tttgaattca ctcacgcccc ctcctt 26

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
tttgaattca tgcatcaaga accgattttt c 31

<210> SEQ ID NO 16
<211> LENGTH: 27
<212> TYPE: DNA
<213> ORGANISM: Artificial Sequence
<220> FEATURE:
<223> OTHER INFORMATION: primer -continued

<400> SEQUENCE: 16

```
tttaagcttt tatttgcttg tccgtgg                                           27
```

MANNOSE-6-PHOSPHATE ISOMERASE, MUTANT THEREOF, AND USE THEREOF

BACKGROUND OF THE INVENTION

1. Field of the Invention

The present invention relates to new mannose-6-phasphate isomerase, mutant enzyme thereof, and a method of producing L-ribose using the enzyme, and more specifically, to mannose-6-phosphate isomerase, mutant enzyme thereof, recombinant expression vectors including relevant genes, microorganisms transformed with the vectors, a method of producing mannose-6-phosphate isomerase or mutant thereof in bulk using them, and a high yield method of producing L-ribose using the mannose-6-isomerase or the mutant thereof.

2. Description of the Related Art

L-ribose is a starting material for the synthesis of many L-type nucleotide sugar drugs and is used to synthesis methyl-L-riboflanoside (Bezimidavir™) that is an antiviral drug, and the like. In addition, the world market for L-ribose and derivatives thereof was approximately 1.1 billion dollars in 2001.

In addition, recently, demand for L-ribose is sharply increasing as a main intermediate of BW1263W94 (Glaxo Wellcome) that is being developed as a new antiherpes, L-FMAU (Bukwang & Triangle) that is being developed as a drug for treating Hepatitis B, and the like. Thus, the development of the industrial available method is at the center of attention by many researchers in the same field.

L-ribose mostly has been produced from L-arabiose, L-xylose, D-glucose, D-galactose, D-ribose, or D-manno-1,4-lactone using a chemical synthesis (Akagi, M., et al., *Chem. Pharm. Bull.* (Tokyo) 50:866, 2002; Takahashi, H., et al., *Org. Lett.* 4:2401, 2002; Yun, M., et al., *Tetrahedron Lett.* 46:5903, 2005). However, the chemical synthesis has many serious problems with the production process.

Actually, the risk of working environment that requires a high temperature and high pressure, complex separating and purifying process of ribose due to a production of additive sugars after the chemical reaction, environmental pollution due to chemical wastes produced during the process, and the like can be caused.

In order to overcome the above-mentioned problems, recently, a method of producing biological L-ribose from libitol or L-ribulose is being researched.

In addition, the conversion rate from 100 g/l of libitol to L-ribose was 55% only after 72 hours of fermentation using recombinant *E. coli* including NAD-dependent mannitol-1-dehydrogenase, but the productivity of L-ribose was approximately 28-fold lower than that of the chemical synthesis from L-arabinose (Woodyer R. N., et al., *Appl. Environ. Microbiol.* 74:2967, 2008; Jumppanen, J., et al., U.S. Pat. No. 6,140, 498).

Meanwhile, a biological researching method of producing L-ribose is using L-arabiose isomerase derived from *Klebsiella pneumonia*, L-rhamnose isomerase derived from *Pseudomonas stutzeri*, D-xylose isomerase derived from *Streptomyces rubiginosus*, and galactose-6-phosphate isomerase derived from *Lactococcus lactis*. However, the above-mentioned enzymes can convert from L-ribulose to L-ribose but their conversion rates are very slow because they have wide substrate specificity.

Recently, the present inventors overcame the problem related to the lower productivity by converting L-ribulose to L-ribose using mannose-6-phosphate isomerase derived from *Bacillus subtilis* (Yeom S. J., et al., *Appl. Environ. Microbiol.* 75:4705, 2009). However, the mannose-6-phosphate isomerase derived from *Bacillus subtilis* is limited to dissolve a great quantity of substrates because it is the enzyme derived from *Mesophilic bacterium* so that it has low thermostability and low reaction temperature. Accordingly, in order to overcome this, it is urgent to develop an economical and biological method for overcoming the limitation of substrate solubility while the method can provide the high productivity of L-ribose and high thermostability.

SUMMARY OF THE INVENTION

The present invention is developed to solve the above-mentioned problems and by the above-mentioned needs, and an object of the present invention is to provide new mannose-6-phosphate isomerase.

Another object of the present invention is to provide mutant of new mannose-6-phosphate isomerase.

Another object of the present invention is to provide a method of producing the mannose-6-phosphate isomerase.

Another object of the present invention is to provide a method of producing the mutant of mannose-6-phosphate isomerase.

Another object of the present invention is to provide a high yield method of producing L-ribose.

In order to achieve the above objects, the present invention provides mannose-6-phosphate isomerase used for producing L-ribose.

According to a preferable embodiment of the present invention, the mannose-6-phosphate isomerase may be preferably derived from various strains, such as *Thermus thermophilus* or *Geobacillus thermodenitrificans*, but the present invention is not limited thereto.

According to a preferable embodiment of the present invention, the isomerase preferably may have the amino acid sequence of Sequence No. 1 or No. 2, but all of the mutant enzymes having the mannose-6-phosphate isomerase activity that is desired by the present invention by inducing at least one of mutation in the above sequence may be included in the right range of the present invention.

Examples of the above-mentioned mutant enzymes are, but are not limited to, as follows:

a) the mutant, in which the amino acid residue, i.e., Arg (R), at position 142 in the mannose-6-phosphate isomerase having Sequence No. 1 is replaced with Asn (N); b) the mutant, in which the amino acid residues, i.e., Lys (K), Asn (N), and Met (M), at positions 21, 74, and 134 in the mannose-6-phosphate isomerase as disclosed in Sequence No. 2 are replaced with Glu (E), Thr (T), and Arg (R), respectively; c) the mutant, in which the amino acid residues, i.e., glu (E) and Thr (T), at positions 67 and 238 in the mannose-6-phosphate isomerase as disclosed in Sequence No. 2 are replaced with Gly (G) and Ile (I), respectively; d) the mutant, in which the amino acid residue, i.e., Lys (K), at position 124 in the mannose-6-phosphate isomerase as disclosed in Sequence No. 2 is replaced with Arg (R); e) the mutant, in which the amino acid residue, i.e., Leu (L), at position 129 in the mannose-6-phosphate isomerase as disclosed in Sequence No. 2 is replaced with Phe (F) or Tyr (Y); f) the mutant of the mannose-6-phosphate isomerase selected from the group consisting of the mutants, in which the amino acid residue, i.e., Asn (N), at position 90 in the mannose-6-phosphate isomerase as disclosed in Sequence No. 2 is replaced with Ala (A), Asp (D), His (H) or Leu (L); and g) the mutant, in which at least two relevant residues are mutated by replacing the original amino acids in at least two relevant residues with at least one of relevant mutation amino acids from b) to f) through a combination of at least one of single point mutation from the above b) to f).

According to another embodiment of the present invention, the mutant of the above g) may preferably be the mutant of mannose-6-phosphate isomerase, in which the amino acid residue, i.e., Asn (N), at position 90 in the mannose-6-phosphate isomerase as disclosed in Sequence No. 2 is replaced with Ala (A) and the amino acid residue, i.e., Leu (L), at position 129 is replaced with Phe (F), but the present invention is not limited thereto.

In addition, the present invention provides gene encoding the enzyme of the present invention.

According to an embodiment of the present invention, the gene may preferably have any one of base sequences selected from Sequence No. 3 or Sequence No. 4. However, considering a degeneration of genetic code, and the like, all of the genes having at least 80% of homology with them and the mannose-6-phosphate isomerase activity that is desired by the present invention, or functional fragments thereof may be also included in the right range of the present invention, and examples of them may include the base sequences as disclosed in Sequence No. 5 to Sequence No. 12, but the present invention is not limited thereto.

In addition, the present invention provides recombinant expression vectors including mannose-6-phosphate isomerase gene having one of base sequences selected from Sequence No. 3 to Sequence No. 12.

According to an embodiment of the present invention, the recombinant expression vector may be preferably expression vector, pET 28(+)a/mannose-6-phosphate isomerase or pTrc 99a/mannose-6-phosphate isomerase, but the present invention is not limited thereto.

In addition, the present invention may provide a method of producing the mannose-6-phosphate isomerase according to the present invention, or mutant enzyme thereof, including:

a) culturing a microorganism transformed with the expression vector according to the present invention; and b) isolating the mannose-6-phosphate isomerase from the microorganism.

In addition, the present invention may provide a method of producing L-ribose using the mannose-6-phosphate isomerase according to the present invention, or mutant thereof.

In addition, the present invention may provide a composition for producing ribose including the mannose-6-phosphate isomerase according to the present invention, or mutant thereof.

The mannose-6-phosphate isomerase gene according to the present invention may be isolated from strains, such as *Thermus thermophilus* or *Geobacillus thermodenitrificans*. Firstly, chromosome DNA may be obtained from the strains, such as *Geobacillus thermodenitrificans* or *Thermus thermophilus* having the mannose-6-phosphate isomerase gene. Next, the planned oligonucleotide may be used as a primer and chromosome DNA of the strain, i.e., *Geobacillus thermodenitrificans* may be used as a template to perform a polymerase chain reaction (PCR) and then amplify partially the mannose-6-phosphate isomerase gene. PCR amplified fragment obtained from the above process has nearly 100% homology with the mannose-6-phosphate isomerase gene of the strain, *Thermus thermophilus* or *Geobacillus thermodenitrificans*. It may be expected to have high S/N ratio as a probe when performing a colony hybridization and also to facilitate a stringency of hybridization. The PCR amplified fragment is marked with a proper reagent, and performed by carrying out the colony-hybridization to the chromosome DNA library to select the mannose-6-phosphate isomerase gene (Current Protocols in Molecular Biology, vol. 1, page 603, 1994).

The DNA fragment including the mannose-6-phosphate isomerase gene can be obtained by recovering plasmid from *E. coli* selected by the above-mentioned method using an alkali method (Current Protocols in Molecular Biology, vol. 1, page 161, 1994). In addition, after determining the base sequence by the above-mentioned method, the whole genes of the present invention can be obtained by hybridizing using the DNA fragment as a probe prepared by cleaving the DNA fragment having the above-mentioned base sequence with restriction enzymes.

The transformed microorganism of the present invention may be obtained by introducing the recombinant vector into the host cell that is suitable for the expression vector used for preparing the recombinant vector. For example, when using bacteria, such as *E. coli* as a host, the recombinant vector according to the present invention may preferably have the following features: preferably, it may be possible to autonomously replicating in the host, itself, and also may have a needed configuration for expressions of a transcription termination factor, DNA including the mannose-6-phosphate isomerase gene, promoter, and the like. The expression vectors used for the present invention may include pET 28(+)a or pTrc 99a, but if the expression vectors meet the requirements as mentioned above, they may be used.

A production of the mutant of the mannose-6-phosphate isomerase according to the present invention may be performed by culturing the transformant obtained by transforming the host by a recombinant vector having the gene encoding it; and producing and accumulating the mannose-6-phosphate isomerase that is a genetic product in a culture (cultured bacteria or cultured supernatant) to obtain the enzyme from the culture.

The obtaining and purifying of the mannose-6-phosphate isomerase according to the present invention may be performed by using a bacteria destruction, an affinity chromatography, a cation or anion ion-exchange chromatography, and the like, along or by combining, after centrifuging and recovering bacteria or supernatant from the obtained culture.

BRIEF DESCRIPTION OF THE DRAWINGS

The above and other aspects, features and other advantages of the present invention will be more clearly understood from the following detailed description taken in conjunction with the accompanying drawings, in which:

FIG. 9 is a genetic sequence of R142N mutant enzyme of mannose-6-phosphate isomerase derived from *Thermus thermophiles* strain as set forth in SEQ ID NO: 5 according to the present invention;

FIG. 10 is a cleavage map of recombinant expression vector including the gene of mannose-6-phosphate isomerase derived from *Thermus thermophilus* strain according to the present invention;

FIG. 17 to FIG. 21 are genetic sequences of Mutant 1(18), Mutant 2(19), Mutant 3(20), and Mutant 4(21), which are mutant enzymes of mannose-6-phosphate isomerase (17) derived from *Geobacillus thermodenitrificans* strain as set forth in SEQ ID NOs: 4, 6, 7, 8 and 11 according to the present invention;

DETAILED DESCRIPTION OF THE PREFERRED EMBODIMENT

Figure 1:
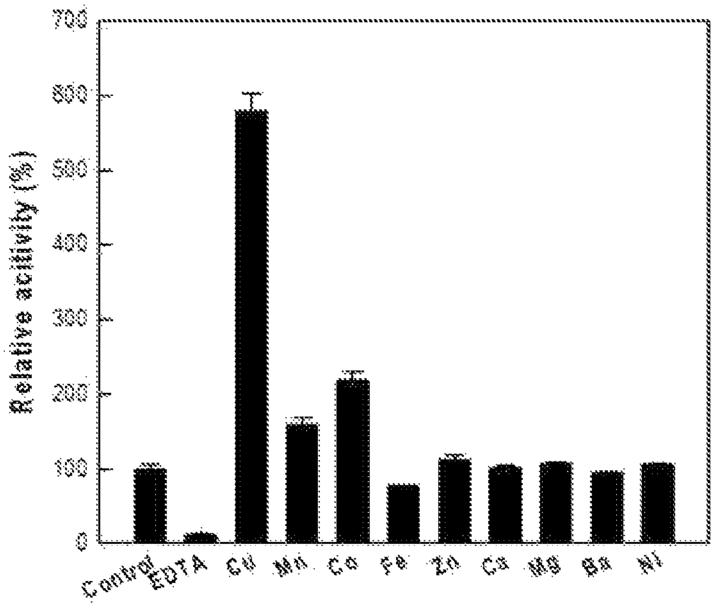
FIG. 1 is an enzyme activity depending on a type of metal ion of mannose-6-phosphate isomerase derived from *Thermus thermophilus* strain according to the present invention.
Figure 2:
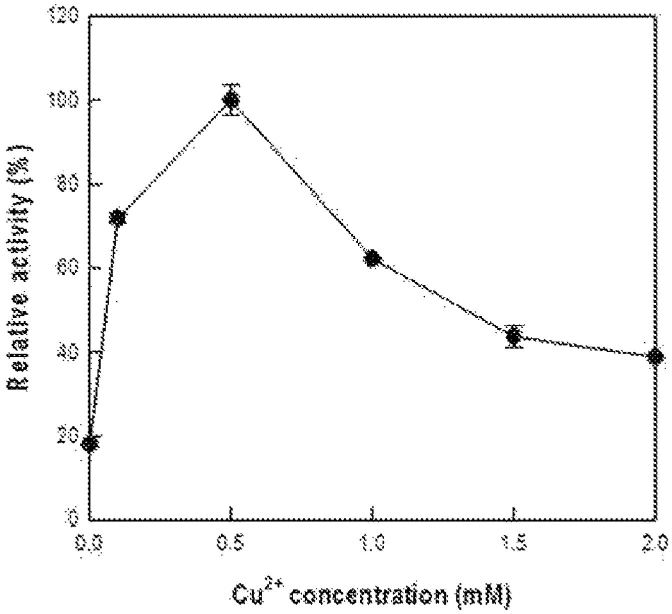
FIG. 2 is an enzyme activity depending on the concentration of the metal ion.

Exemplary embodiments of the present invention will now be described in detail with reference to the accompanying drawings.

Hereinafter, the present invention will be described in more detail with reference to Examples. Examples are only for illustrating the present invention, and thus it is obvious by those of skill in the art that the range of the present invention is not considered to limit the present invention.

Example 1

Production of Transformed Microorganism and Recombinant Expression Vector Including Mannose-6-Phosphate Isomerase Gene 1-1: Mannose-6-Phosphate Isomerase Derived From *Thermus thermophilus* Strain In order to produce mannose-6-phosphate isomerase according to the present invention, mannose-6-phosphate isomerase derived from *Thermus thermophilus* strain was first isolated.

Specifically, *Thermus thermophilus* KCCM 40897 strain, in which its genetic base sequence and amino acid sequence are already specified, was selected, and the following primers were designed based on the known DNA base sequence (Genebank Accession No. AP008226) of the mannose-6-phosphate isomerase derived from the above strain:

```
Sequence No. 13 (Forward Primer):
5'-TTTCATATGAGGCGGTTGGAGCCCAA-3'

Sequence No. 14 (Reverse Primer):
5'-TTTGAATTCACTCACGCCCCCTCCTT-3'
```

The primers were designed to introduce the Nde I and EcoR I restriction sites, respectively, and then the base sequences of relevant genes were amplified by performing a polymerase chain reaction (PCR) using the above primers.

The mannose-6-phosphate isomerase gene that was obtained in bulk was inserted into a plasmid vector, pET 28(+) (available from Novagen) using the restriction enzymes, Nde I and EcoR I to prepare pET 28(+)a/mannose-6-phosphate isomerase.

The recombinant expression vector that was obtained as mentioned above was transformed into *E. coli* ER 2566 strain by a general transformation method, and then the transformed microorganism was frozen before performing a culture for producing L-ribose by adding 20% glycerine solution.

1-2: Mannose-6-Phosphate Isomerase Derived From *Geobacillus thermodenitrificans* Strain In order to produce mannose-6-phosphate isomerase, mannose-6-phosphate isomerase derived from *Geobacillus thermodenitrificans* strain was first isolated.

Specifically, *Geobacillus thermodenitrificans* strain, in which its genetic base sequence and amino acid sequence are already specified, was selected (Dae-Heoun Baek, Yujin Lee, Hong-Sig Sin, and Deok-Kun (2004) *J Microbiol. Biotechnol.* 14: 312-316), and the following primers were designed based on the known DNA base sequence (Genebank Accession Number CP000557) of the mannose-6-phosphate isomerase derived from the above strain:

```
Mannose-6-Phosphate Isomerase
Sequence No. 15 (Forward Primer):
5'-TTTGAATTCATGCATCAAGAACCGATTTTTC-3'

Sequence No. 16 (Reverse Primer):
5'-TTTAAGCTTTTATTTGCTTGTCCGTGG-3'
```

The primers of the mannose-6-phosphate isomerase gene were designed to introduce the EcoR I and Hind III restriction sites. The base sequences of relevant genes were amplified by performing a polymerase chain reaction (PCR) using the above primers. The mannose-6-phosphate isomerase gene that was obtained in bulk was inserted into a plasmid vector, pTRC 99a (available from Novagen) using each of the restriction enzymes to prepare pTRC 99a/mannose-6-phosphate isomerase.

The recombinant expression vector that was obtained as mentioned above was transformed into *E. coli* ER 2566 strain by a general transformation method, and then the transformed microorganism was frozen before performing a culture for producing L-Ribose by adding 20% glycerine solution.

Example 2

Preparation of Mannose-6-Phosphate Isomerase

In order to produce the mannose-6-phosphate isomerase according to the present invention in bulk, the recombinant *E. coli* ER 2566 strain that was frozen was inoculated to a test tube including 3 ml of LB medium. And then, the seed culture was performed at 37° C. on a plate shaker until its absorbance was to be 2.0 at 600 nm. Since then, the seed culture solution was added to 2,000 ml flask including 500 ml of LB medium and then the main culture was performed.

In addition, 0.1 mM IPTG was added until its absorbance was to be 0.6 at 600 nm to induce the bulk expression of mannose-6-phosphate isomerase. At this point, it was maintained to be 200 rpm of the shaking rate and 37° C. of culturing temperature, and was cultured after the shaking rate and culturing temperature were adjusted to 150 rpm and 16° C., respectively, after adding IPTG.

In addition, the mannose-6-phosphate isomerase that was over-expressed as mentioned above was isolated as an enzyme solution used for producing L-ribose as the following procedure:

The culture solution of transformed strain was centrifuged at 6,000×g for 30 minutes at 4° C., and then washed twice with 0.85% sodium chloride (NaCl). Since then, 50 mM sodium phosphate, 300 mM sodium chloride, 10 mM immidazole, and 0.1 mM proteinase inhibitor (phenylmethylsulfonyl fluoride) were added and then the lysis of the cell solution was performed with a sonicator. The cell lysate was again centrifuged at 13,000×g for 20 minutes at 4° C. to remove the cell pellet and obtain only the cell supernatant. Since then, the mannose-6-phosphate isomerase was isolated from the cell supernatant as an enzyme solution used for producing L-ribose by installing Histrap HP absorption column using His-tag to a fast protein liquid chromatography system (BIO-RAD Laboratories, Hercules, Calif., USA).

Example 3

Investigation of Metal Specificity of Mannose-6-Phosphate Isomerase

In order to investigate specificities of the mannose-6-phosphate isomerase obtained from the Example 2 to metal ions, after 10 mM EDTA was treated and then metal ions ($Mn^{2+}$, $Zn^{2+}$, $Ba^{2+}$, $Cu^{2+}$, $Co^{2+}$, $Mg^{2+}$, $Ni^{2+}$, $Fe^{2+}$) were treated, the activity of the enzyme was measured as follows:

The enzyme reaction was performed at 75° C. for 5 minutes using 50 mM PIPES (piperazine-N,N'-bis(2-ethane sulfonic acid)) buffer solution (pH 7.0) including 10 mM L-ribulose, each of the metal ions, and 0.05 unit/ml enzyme, and then stopped by adding a final concentration of 200 mM hydrogen chloride (HCl).

In the present invention, the enzyme activity was measured by using L-ribulose as a substrate, and one unit of the enzyme activity was defined as the amount of enzyme required to produce 1 μmol of L-ribose per 1 minute at 75° C. and pH 7.0 for a comparative analysis.

In addition, when measuring the enzyme activity, the analysis of the concentrations of ribose and ribulose, and other sugars was performed by using Bio liquid chromatography (Bio-LC) system (DIONEX ICS-3000, Sunnylvale, Calif., USA) installed with CarboPacPA and an electrochemical detector, and at this point, 200 mM sodium hydroxide (NaOH) was passed through the CarboPacPA column at the rate of 1 ml/min at 30° C.

In addition, when measuring the enzyme activity, the analysis of the concentrations of ribose and ribulose, and other sugars was performed by using Bio liquid chromatography (Bio-LC) system (Dionex ICS-3000, Sunnylvale, Calif., USA) installed with CarboPacPA and an electrochemical detector, and at this point, 200 mM sodium hydroxide (NaOH) was passed through the CarboPacPA column at the rate of 1 ml/min at 30° C.

As a result, there were no activities of the purified enzyme and EDTA-treated enzyme, but the mannose-6-phosphate isomerase derived from *Thermus thermophilus* strain was most effectively stimulated by copper ($Cu^{2+}$) among the metal ions used for the experiment and the optimum concentration confirmed from the result of experiment per concentration was 0.5 mM and the mannose-6-phosphate isomerase derived from *Geobacillus thermodenitrificans* strain was most effectively stimulated by cobalt ($Co^{2+}$) and all of the optimum concentrations to the enzyme confirmed from the result of experiment per concentration was 1 mM.

From the above results, it has been seen that the mannose-6-phosphate isomerase according to the present invention may be affected by the metal ion, i.e., copper or cobalt and thus may be metal ion-dependent enzyme (see FIGS. 1, 2, 11, & 12).

Example 4

Investigation of Activity of Mannose-6-Phosphate Isomerase

In order to investigate activity of the mannose-6-phosphate isomerase obtained from the above Example 2 according to the change of temperature and pH, the enzyme activities were compared by reacting the enzyme and substrate under various pHs and temperatures conditions.

4-1. Effect of pH on Activity of Mannose-6-Phosphate Isomerase

Firstly, in order to investigate an effect of pH on the enzyme activity, the enzyme reaction was performed at the range from pH 7.5 to pH 8.5 using EPPS(N-(2-hydroxyethyl) piperazine-N-(3-propane sulfonic acid)) buffer including 0.05 unit/ml enzyme, 10 mM L-ribulose as a substrate, and 0.5 mM copper (or 1 mM cobalt: in the case of *Geobacillus*) and 50 mM PIPES buffer including 1.5 unit (or 2 unit: in the case of *Geobacillus*)/ml enzyme, 0.5 mM copper (or 1 mM cobalt: in the case of *Geobacillus*), and 10 mM L-ribulose as a substrate, and specifically, was performed at 75° C. for 5 minutes and then a final concentration of 200 mM hydrogen chloride was again added to stop the reaction.

Figure 3:
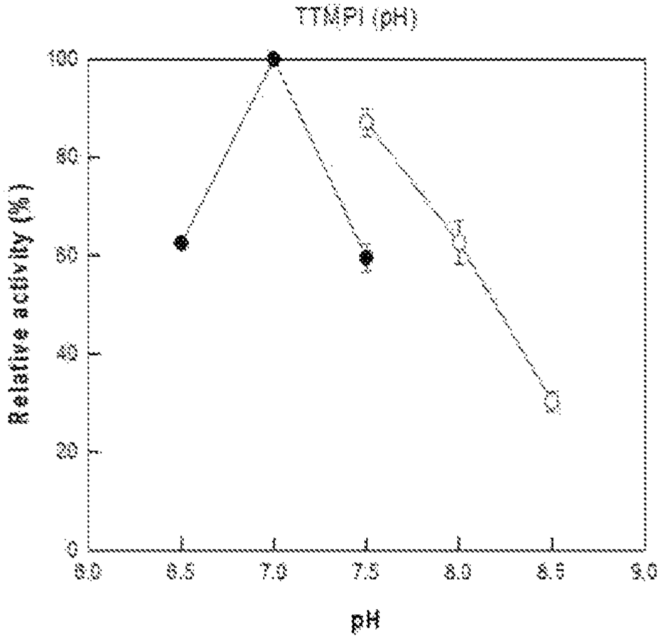
FIG. 3 is an enzyme activity depending on pH of mannose-6-phosphate isomerase derived from *Thermus thermophilus* strain according to the present invention (●: PIPES buffer; ○: EPPS buffer)
Figure 13:
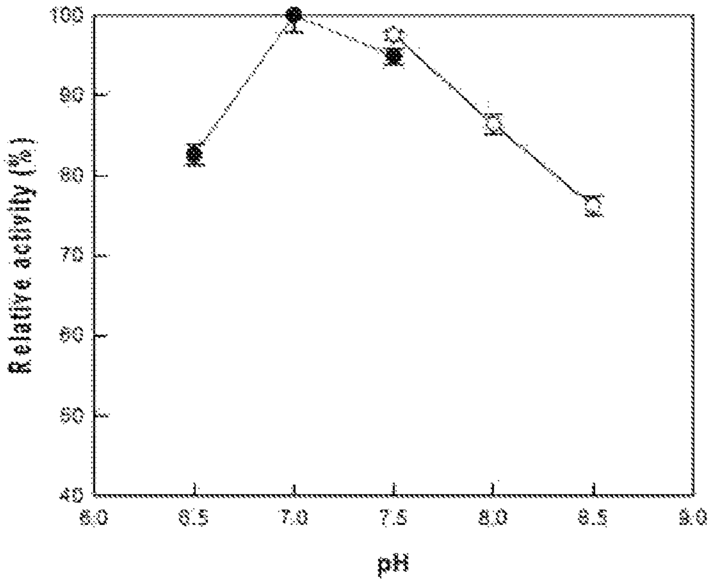
FIG. 13 is a result of comparing enzyme activities depending on pH of mannose-6-phosphate isomerase derived from *Geobacillus thermodenitrificans* strain according to the present invention.

As a result, it has been seen that the optimum pH was 7.0 (see FIGS. 3 & 13).

4-2. Effect of Temperature on Activity of Mannose-6-Phosphate Isomerase

In order to investigate an effect of temperature on the enzyme activity, the reactions were performed for 20 minutes using 50 mM PIPES buffer including 1.5 unit (or 2 unit: in the case of *Geobacillus*)/ml enzyme, 0.5 mM copper (or 1 mM cobalt: in the case of *Geobacillus*), and 10 mM L-ribulose at the range from 60° C. to 90° C. of the enzyme reaction temperature, respectively.

Figure 4:
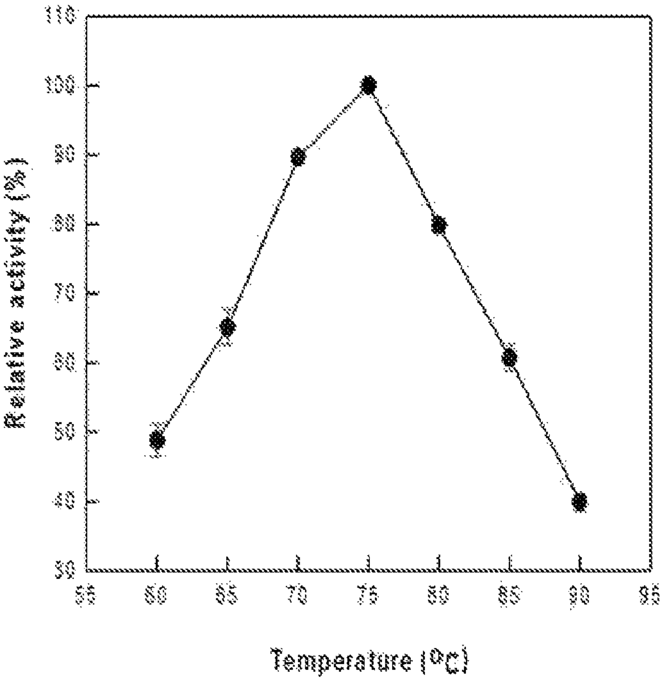
FIG. 4 is an enzyme activity depending on temperatures.
Figure 14:
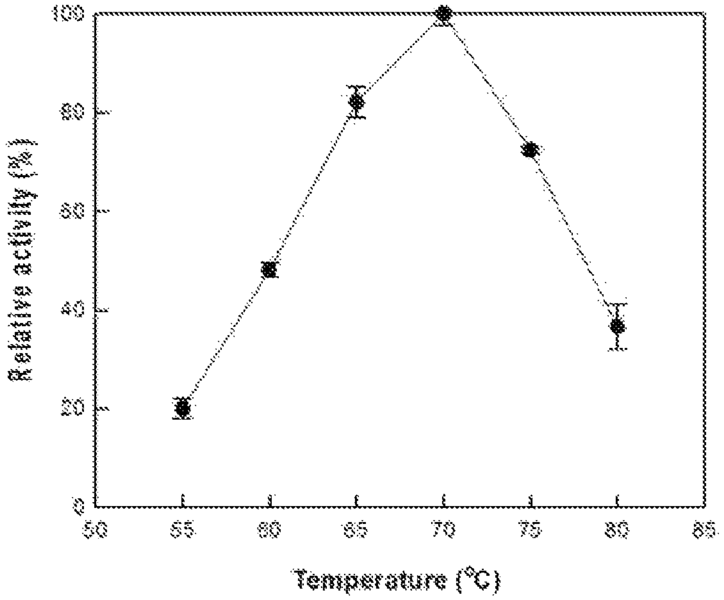
FIG. 14 is a result of comparing enzyme activities of mannose-6-phosphate isomerase derived from *Geobacillus thermodenitrificans* strain according to the present invention depending on temperature.

As a result, it has been seen that the optimum temperature was 70° C. in the case of *Geobacillus* and 75° C. in the case of *Thermus*, respectively (see FIGS. 4 & 14).

4-3. Investigation of Thermostability of Mannose-6-Phosphate Isomerase

In order to investigate thermostability of the enzyme, the reaction was performed using 50 mM PIPES buffer of pH 7.0 including 0.05 unit/ml enzyme, 0.5 mM copper (or 1 mM cobalt: in the case of *Geobacillus*), and 10 mM L-ribulose at the temperature range from 65° C. to 85° C. for the time required until the enzyme activity was down by half, respectively, and then a final concentration of 200 mM hydrogen chloride was added to stop the reaction and then measure the activity of mannose-6-phosphate isomerase.

Figure 5:
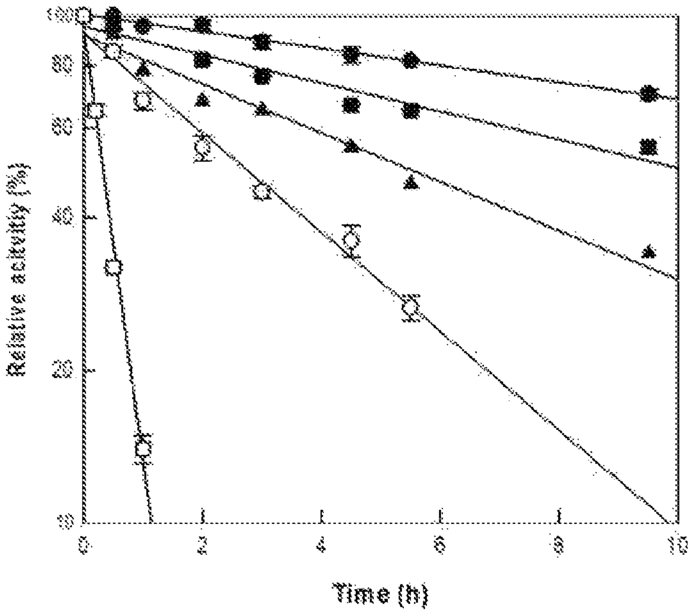
FIG. 5 is a result of measuring thermostability of mannose-6-phosphate isomerase derived from *Thermus thermophilus* strain according to the present invention (●: 65° C.; ■: 70° C.; ▲: 75° C.; ○: 80° C.; and □: 85° C.)

As a result, it has been seen that the activity of mannose-6-phosphate isomerase derived from *Thermus thermophilus* strain was down by half after 22 hours, 10 hours, 5.5 hours, 2.2 hours, and 0.3 hours at the temperatures of 65° C., 70° C., 75° C., 80° C., and 85° C., respectively (see FIG. 5).

Figure 15:
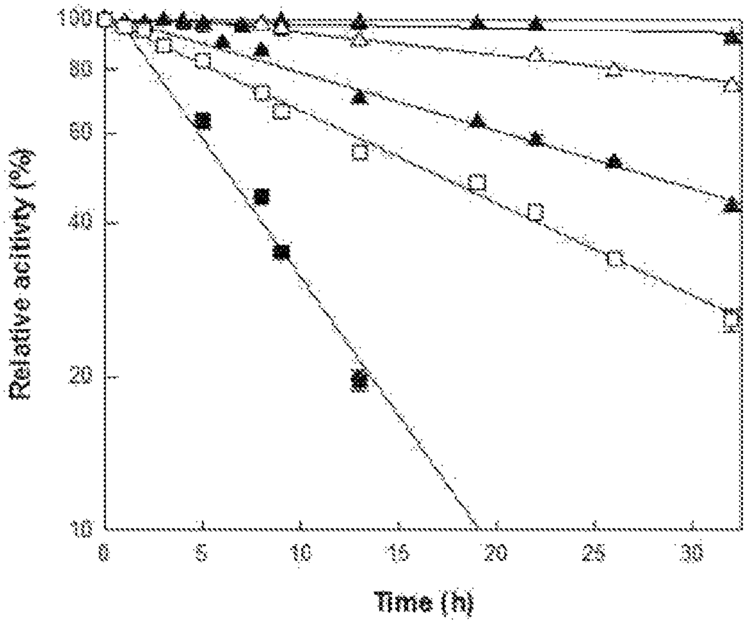
FIG. 15 is a result of measuring stabilities of mannose-6-phosphate isomerase derived from *Geobacillus thermodenitrificans* strain according to the present invention depending on temperatures.

In addition, as shown in FIG. 15, it has been seen that the activity of mannose-6-phosphate isomerase derived from *Geobacillus thermodenitrificans* strain was down by half after 338 hours, 73 hours, 27 hours, 17 hours, and 6.2 hours at the temperatures of 60° C., 65° C., 70° C., 75° C., and 80° C., respectively.

4-4. Effect of Substrate Concentration on Activity of Mannose-6-Phosphate Isomerase In order to investigate an effect of temperature on the enzyme activity, the reaction was performed for 3 hours using 50 mM PIPES buffer of pH 7.0 including 20 unit/ml enzyme, 0.5 mM copper (or 1 mM cobalt: in the case of *Geobacillus*), and 50, 100, 200, and 300 g/l of L-ribulose at the temperature range from 75° C. to 85° C., and then a final concentration of 200 mM hydrogen chloride was added to stop the reaction and then measure the activity of mannose-6-phosphate isomerate.

As a result, in the case of mannose-6-phosphate isomerase derived from *Thermus thermophiles* strain, all of the conversion rates were approximately 70% regardless the concentrations of L-ribulose used as a substrate thereby producing 36, 71, 140, and 211 g/l of L-ribose at 50, 100, 200, and 300 g/l of L-ribulose, respectively.

Example 5

Production of L-Ribose Using Mannose-6-Phosphate Isomerase

In order to confirm productivity of L-ribose using the mannose-6-phosphate isomerase according to the present invention, the output of producing L-ribose by the hour was measured using 300 g/l of L-ribulose as a substrate at 75° C. of the temperature considering the time required until the enzyme activity was down by half and pH 7.0 that was the optimum pH of enzyme confirmed as mentioned above. At this time, the reaction solution used was 50 mM PIPES buffer of pH 7.0 including 25 unit/ml enzyme, 0.5 mM copper, and 300 g/l of L-ribulose.

Figure 6:
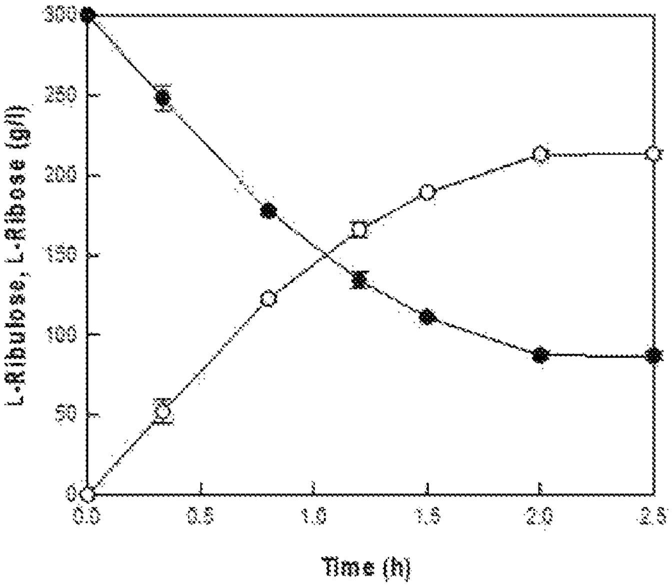
FIG. 6 is a producing output of L-ribose by the hour using mannose-6-phosphate isomerase derived from *Thermus thermophilus* strain according to the present invention.

In the case of the enzyme derived from *Thermus thermophilus* strain, 213 g/l of L-ribose was produced from 300 μg of L-ribulose after 2.5 hours of the reaction, which means that the productivity was 85.2 g/l and the conversion rate was 71%, per hour (see FIG. 6).

Figure 16:
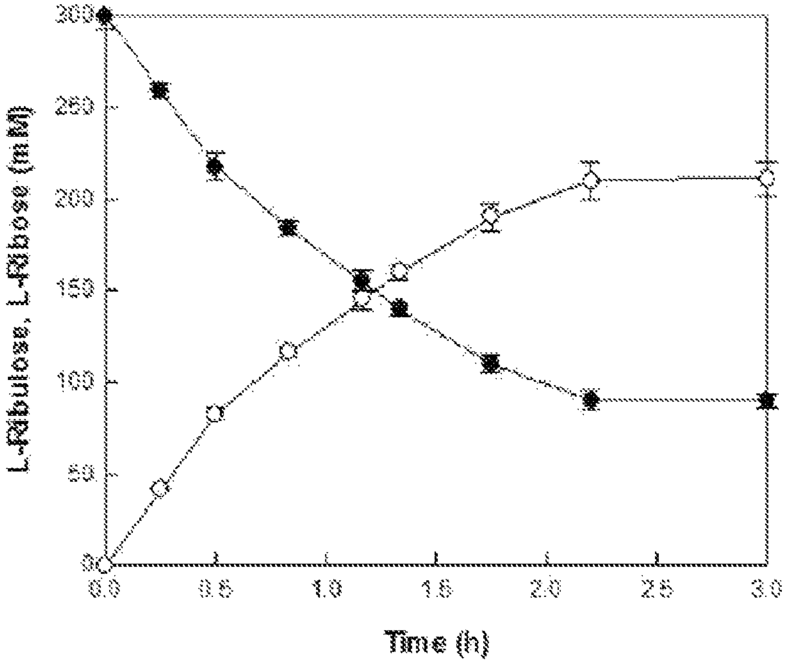
FIG. 16 is a producing output of ribose using mannose-6-phosphate isomerase derived from *Geobacillus thermodenitrificans* strain according to the present invention at 300 g/l of substrate concentration.
Figure 22:
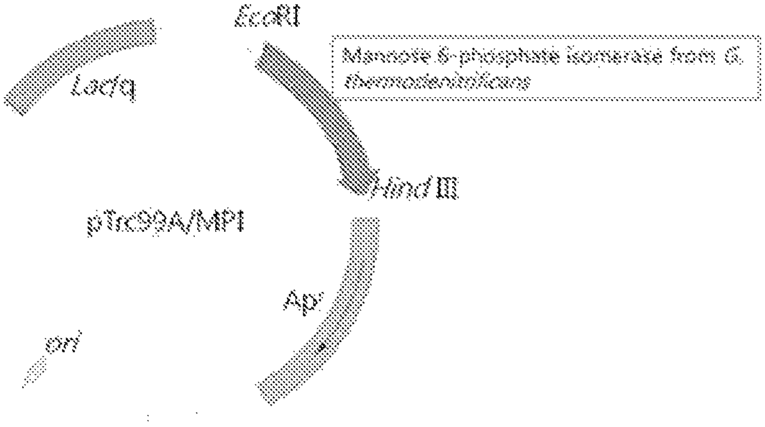
FIG. 22 is a cleavage map of expression vector including the gene of mannose-6-phosphate isomerase derived from *Geobacillus thermodenitrificans* strain.

In addition, in the case of the enzyme derived from *Geobacillus thermodenitrificans* strain, 210 g/l of L-ribose was produced from 300 μg of L-ribulose after 2.2 hours of the reaction, which means that the productivity was 87.5 g/l and the conversion rate was 70%, per hour (see FIG. 16).

Up to now, the chemical synthesis using Molybdic acid exhibited the highest productivity among the productions of ribose, which means that it exhibited 23% of the conversion rate from L-arbinose and 20 g/l productivity per hour (Jumppanen, J., J. Nurmi, and O. Pastinen. October 2000. Process for the continuous production of high purity of L-ribose. U.S. Pat. No. 6,140,498.).

Example 6

Preparation of Transformed Microorganism and Recombinant Expression Vector Including Mannose-6-Phosphate Isomerase Gene and Mutant Thereof 6-1: Mannose-6-Phosphate Isomerase Mutant Derived From *Thermus thermophilus* Strain In order to prepare mannose-6-phosphate isomerase, mannose-6-phosphate isomerase derived from *Thermus thermophilus* strain was first isolated.

Specifically, *Thermus thermophilus* KCCM 40897 strain, in which its genetic base sequence and amino acid sequence are already specified, was selected, and the primers were designed based on the known DNA base sequence (Genebank Accession No. AP008226) of the mannose-6-phosphate isomerase derived from the above strain.

The primers were designed to introduce the Nde I and EcoR I restriction sites. The base sequences of relevant genes were amplified by performing a polymerase chain reaction (PCR) using the above primers. The mannose-6-phosphate isomerase gene that was obtained in bulk was inserted into a plasmid vector, pET 28(+) (available from NOVAGEN) using the restriction enzymes, Nde I and EcoR I to prepare pET 28(+)a/mannose-6-phosphate isomerase.

The primers were designed in order to prepare the mutation vector of the mannose-6-phosphate isomerase (see Table 1). pET 28(+)a/mannose-6-phosphate isomerase mutation vector was prepared by inducing the mutation using the above primers and Quick-Change kit (Stratagene, Beverly, Mass.).

The recombinant expression vector that was obtained as mentioned above was transformed into *E. coli* ER 2566 strain by a general transformation method. In addition, the transformed microorganism was frozen before performing a culture for producing L-Ribose by adding 20% glycerine solution.

TABLE 1

| Mutant Enzyme | Primers | |
|---|---|---|
| R142A | F: CGGACCTCACCTACGCCCTCTACGACTACG | (SEQ ID NO: 17) |
| | R: CGTAGTCGTAGAGGGCGTAGGTGAGGTCCG | (SEQ ID NO: 18) |
| R142K | F: TCGGACCTCACCTACAAGCTCTACGACTACGGCAGGC | (SEQ ID NO: 19) |
| | R: GCCTGCCGTAGTCGTAGAGCTTGTAGGTGAGGTCCGA | (SEQ ID NO: 20) |
| R142N | F: TCGGACCTCACCTACAATCTCTACGACTACGGCAGGC | (SEQ ID NO: 21) |
| | R: CCTGCCGTAGTCGTAGAGATTGTAGGTGAGGTCCGA | (SEQ ID NO: 22) |
| R142E | F: TCGGACCTCACCTACGAACTCTACGACTACGGCAGGC | (SEQ ID NO: 23) |
| | R: GCCTGCCGTAGTCGTAGAGTTCGTAGGTGAGGTCCGAC | (SEQ ID NO: 24) |
| R142Y | F: TCGGACCTCACCTACTACCTCTACGACTACGGCAGGC | (SEQ ID NO: 25) |
| | R: GCCTGCCGTAGTCGTAGAGGTAGTAGGTGAGGTCCGA | (SEQ ID NO: 26) |

Table 1 shows the primers in order to prepare the mutation vectors of the mannose-6-phosphate isomerase.

6-2: Mannose-6-Phosphate Isomerase Mutant Derived From *Geobacillus thermodenitrificans* Strain pTrc99a/mannose-6-phosphate isomerase mutation vector was prepared using PCR mutagenesis kit (CLONTECH Laboratories, Palo Alto. Calif., USA) in order to induce a random mutagenesis of the mannose-6-phosphate isomerase derived from *Geobacillus thermodenitrificans* strain.

The recombinant expression vector that was obtained as mentioned above was transformed into *E. coli* ER 2566 strain by a general transformation method. In addition, the transformed microorganism was frozen before performing a culture for producing L-Ribose by adding 20% glycerine solution.

Example 7

Preparation of Mannose-6-Phosphate Isomerase and Mutant Enzyme 7-1: Mannose-6-Phosphate Isomerase Mutant Derived From *Thermus thermophilus* Strain In order to produce the mannose-6-phosphate isomerase and mutant enzyme in bulk, the recombinant *E. coli* ER 2566 strain that was prepared in the above Example 6 and then frozen was inoculated to a test tube including 3 ml of LB medium. And then, the seed culture was performed at 37° C. on a plate shaker until its absorbance was to be 2.0 at 600 nm. Since then, the seed culture solution was added to 2,000 in flask including 500 ml of LB medium and then the main culture was performed. In addition, 0.1 mM IPTG was added until its absorbance was to be 0.6 at 600 nm to induce the bulk expression of mannose-6-phosphate isomerase. In the above process, it was adjusted to be maintained at 200 rpm of the shaking rate and 37° C. of culturing temperature, and was cultured after the shaking rate and culturing temperature were adjusted to 150 rpm and 16° C., respectively, after adding IPTG.

In addition, the mannose-6-phosphate isomerase that was over-expressed as mentioned above was isolated as an enzyme solution used for producing L-ribose as the following procedure:

The culture solution of transformed strain was centrifuged at 6,000×g for 30 minutes at 4° C., and then washed twice with 0.85% sodium chloride (NaCl). Since then, 50 mM sodium phosphate, 300 mM sodium chloride, 10 mM immidazole, and 0.1 mM proteinase inhibitor (phenylmethylsulfonyl fluoride) were added and then the lysis of the cell solution was performed with a sonicator. The cell lysate was again centrifuged at 13,000×g for 20 minutes at 4° C. to remove the cell pellet and obtain only the cell supernatant. Since then, the mannose-6-phosphate isomerase was isolated from the cell supernatant as an enzyme solution used for producing L-ribose by installing Histrap HP absorption column using His-tag to a fast protein liquid chromatography system (BIO-RAD Laboratories, Hercules, Calif., USA).

7-2: Mannose-6-Phosphate Isomerase Mutant Derived from *Geobacillus thermodenitrificans* Strain In order to produce the mannose-6-phosphate isomerase mutant derived from *Geobacillus thermodenitrificans* strain in bulk, the recombinant *E. coli* ER 2566 strain that was prepared in the above Example 5 and then frozen was inoculated to a test tube including 3 in of LB medium. And then, the seed culture was performed at 37° C. on a plate shaker until its absorbance was to be 2.0 at 600 nm. Since then, the seed culture solution was added to 2,000 in flask including 500 ml of LB medium and then the main culture was performed. In addition, 0.1 mM IPTG was added until its absorbance was to be 0.6 at 600 nm to induce the bulk expression of mannose-6-phosphate isomerase. In the above process, it was adjusted to be maintained at 200 rpm of the shaking rate and 37° C. of culturing temperature, and was cultured for 5 hours under the same condition after adding IPTG.

In addition, the mannose-6-phosphate isomerase that was over-expressed as mentioned above was isolated as an enzyme solution used for producing L-ribose as the following procedure:

The culture solution of transformed strain was centrifuged at 6,000×g for 30 minutes at 4° C., and then washed twice with 0.85% sodium chloride (NaCl). Since then, 50 mM PIPES (pH 7.0) buffer solution and 0.1 mM proteinase inhibitor (phenylmethylsulfonyl fluoride) were added and then the lysis of the cell solution was performed with a sonicator. The cell lysate was again centrifuged at 13,000×g for 20 minutes at 4° C. to remove the cell pellet and obtain only the cell supernatant. Since then, the mannose-6-phosphate isomerase was isolated from the cell supernatant as an enzyme solution used for producing L-ribose by installing Hi Trap™ HP absorption column that was an anion resin to a fast protein liquid chromatography system (BIO-RAD Laboratories, Hercules, Calif., USA).

Example 8

Specific Activity and Kinetic Parameter of Mannose-6-Phosphate Isomerase and Mutant Enzyme to L-Ribulose 8-1: Mannose-6-Phosphate Isomerase Mutant Derived From *Thermus thermophilus* Strain The experiment for measuring and comparing specific activities of the mannose-6-isomerase and mutant enzyme to L-ribulose was performed.

The enzyme reaction was performed at 75° C. for 5 minutes using 50 mM PIPES buffer solution (pH 7.0) including 10 mM ribulose and the metal ion of 0.5 mM $Cu^{2+}$ and then again stopped by adding a final concentration of 200 mM hydrogen chloride. In the present invention, the enzyme activity was measured by using ribose as a substrate, and one unit of the enzyme activity was defined as the amount of enzyme required to produce 1 nmole of L-Ribose per 1 minute at 75° C. and pH 7.0 for a smooth comparative analysis. In addition, when measuring the enzyme activity, the analysis of the concentrations of ribose and ribulose, and other sugars was performed by using Bio liquid chromatography (Bio-LC) system (DIONEX ICS-3000, Sunnylvale, Calif., USA) installed with CarboPacPA and an electrochemical detector. At this point, 200 mM sodium hydroxide (NaOH) was passed through the CarboPacPA column at the rate of 1 ml/min at 30° C.

The result showed that the activity was increased by 1.4-fold when using L-ribulose as a substrate using R142N mutant enzyme as compared to the wide enzyme. From the result of performing kinetic experiment thereof, it has been seen that the catalytic efficiency of R142N mutant enzyme was 579 $mM^{-1}s^{-1}$, which means that it was increased by 1.5-fold as compared to the wild enzyme having 374 $mM^{-1}s^{-1}$ of the catalytic efficiency. It has been seen that the above value was the highest value among the enzyme reactions for converting from L-ribulose to L-ribose up to now (see Table 2).

TABLE 2

| Enzymes | Specific activity (U/mg) | $K_z$(mH) | $k_{cat}$($s^{-1}$) | $k_{cat}/K_m$ ($mM^{-1}s^{-1}$) |
|---|---|---|---|---|
| Wild | 1493 ± 25 | 136 ± 4 | 50644 ± 709 | 374 ± 11 |
| R142A | 1540 ± 13 | 184 ± 5 | 64873 ± 908 | 353 ± 11 |
| R142N | 2152 ± 37 | 140 ± 4 | 81063 ± 1329 | 579 ± 20 |
| R142K | 1214 ± 18 | 228 ± 6 | 68877 ± 964 | 302 ± 9 |
| R142E | 1045 ± 11 | 151 ± 5 | 32666 ± 536 | 216 ± 8 |
| R142Y | 1092 ± 6.7 | 308 ± 6 | 56178 ± 865 | 182 ± 5 |

Table 2 shows the specific activities and kinetic parameters of the mannose-6-phosphate isomerase and mutant enzyme thereof to L-ribulose.

8-2: Mannose-6-Phosphate Isomerase Mutant Derived From *Geobacillus thermodenitrificans* Strain The experiment for measuring and comparing enzyme activities of the mannose-6-isomerase derived from *Geobacillus thermodenitrificans* stain and mutant thereof to L-ribulose was performed.

The enzyme reaction was performed at 70° C. for 5 minutes using 50 mM PIPES buffer solution (pH 7.0) including 10 mM ribulose and the metal ion of 1 mM $Co^{2+}$ and then again stopped by adding a final concentration of 200 mM hydrogen chloride. In the present invention, the enzyme activity was measured by using L-ribulose as a substrate, and one unit of the enzyme activity was defined as the amount of enzyme required to produce 1 nmole of Ribose per 1 minute at 70° C. and pH 7.0 for a smooth comparative analysis. In addition, when measuring the enzyme activity, the analysis of the concentrations of ribose and ribulose, and other sugars was performed by using Bio liquid chromatography (Bio-LC) system (DIONEX ICS-3000, Sunnylvale, Calif., USA) installed with CarboPacPA and an electrochemical detector. At this point, 200 mM sodium hydroxide was passed through the CarboPacPA column at the rate of 1 ml/min at 30° C.

The result showed that the activities were increased by 1.2~1.4-fold when using L-ribulose as a substrate using four mutant enzymes as compared to the wide enzyme. At this time, it has been seen that the specific activity of the wide enzyme to L-ribulose was 504 U/mg (see Table 3). From the result of comparing the DNA base sequence and amino acid sequence of the mutant enzyme with those of the wide enzyme, it has been seen that the mutations of 1~3 points were confirmed. It has been seen that the mannose-6-phosphate isomerase derived from *Geobacillus thermodenitrificans* strain exhibited the highest productivity of ribose up to now, but the mutant enzyme thereof exhibited much more higher activity than it. This means that the mutant enzyme is the enzyme for producing L-ribose that is superior to the mannose-6-phosphate isomerase derived *Geobacillus thermodenitrificans* having the highest productivity in producing biological L-ribose reported.

TABLE 3

| Enzyme | Mutation point | Relative activity (%) |
|---|---|---|
| Wild | None | 100 |
| Mutant 1 | K21E, N74T, M134R | 121 |
| Mutant 2 | E67G, T238I | 132 |
| Mutant 3 | K124R, L129F | 131 |
| Mutant 4 | N90D | 125 |

Table 3 shows the enzyme activity of mannose-6-phosphate isomerase and mutant enzymes to L-ribulose.

8-3: Another Mannose-6-Phosphate Isomerase Mutant Derived from *Geobacillus thermodenitrificans* Strain Among the high activity-residues obtained by screening the mannose-6-phosphate isomerase derived from *Geobacillus thermodenitrificans* stain, two highest activity-residues were substituted with other amino acids, respectively, to select the highest activity-residue.

Specifically, N90 residue and L129 residue were converted to the amino acids having each different property, and then point mutations were performed to be N90A, N90D, N90E, N90H, N90K, N90L, N90Y, L129A, L129F, L129H, L129W, and L129Y. And then, their activities were compared to the mannose-6-phosphate isomerase derived from the conventional wide-type *Geobacillus thermodenitrificans* strain.

Figure 23:
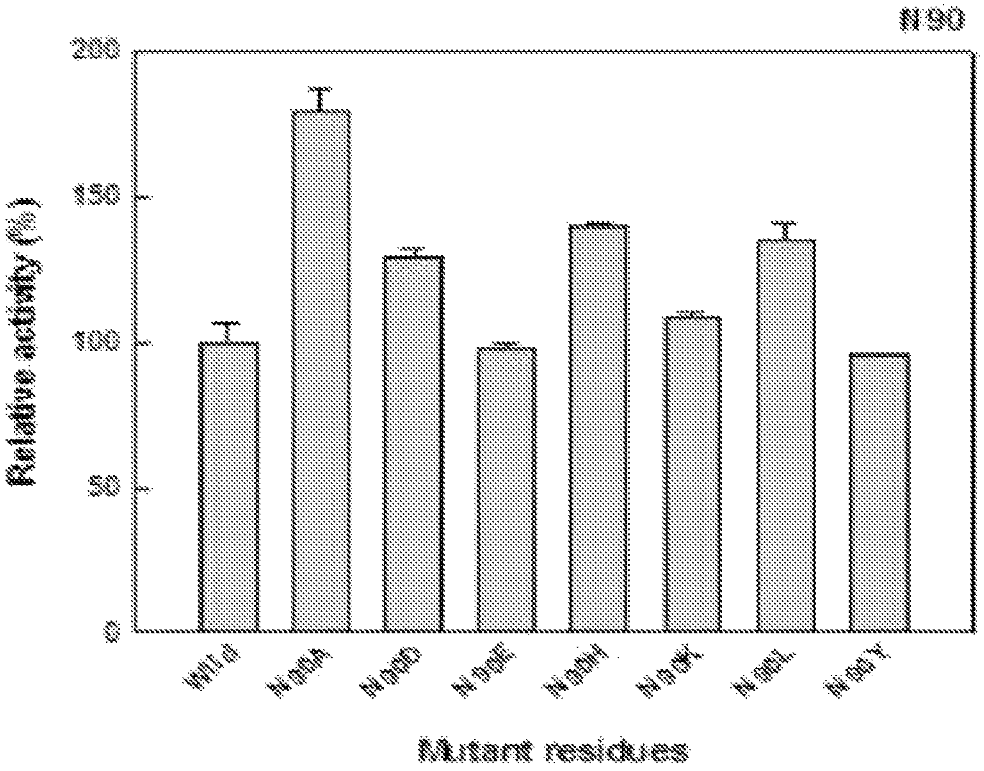
FIG. 23 and FIG. 24 are relative activities of point mutants substituted at amino acid residue at positions 90 (FIG. 23) and 129 (FIG. 24) in the point mutants as compared to the wide type.
Figure 24:
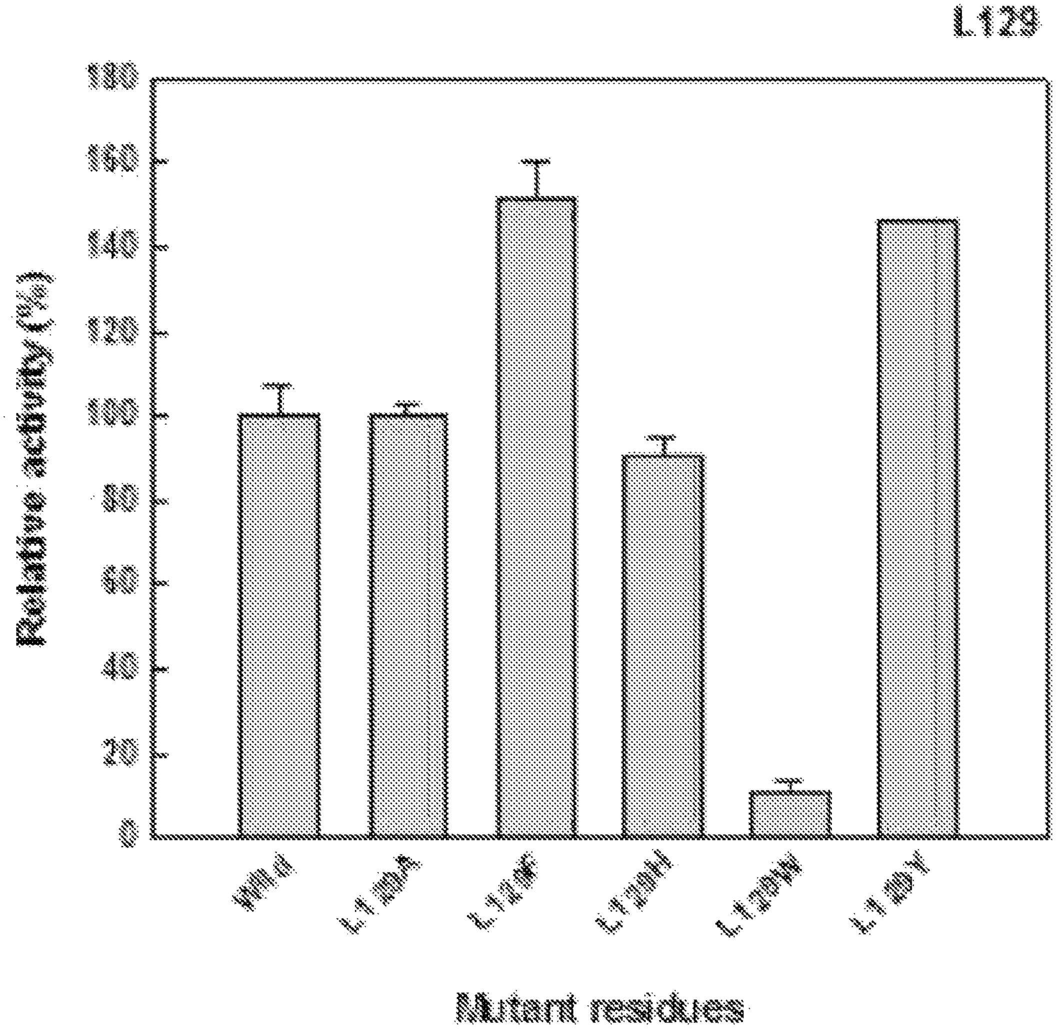

The screening of the present invention was performed using Ketose assay by carrying out an error prone PCR with CLONTECH Diversify PCR Random Mutagenesis Kit. The obtained mutant was replaced with one residue, respectively, substituted with another amino acid, or performed with two mutations, using QuikChange Site-Directed Mutagenesis Kit available from STRATAGENE. In addition, the activities were compared with the conventional MPi. The reactions were compared by measuring specific activities by reacting 0.5 mg/ml of enzyme including 1 mM $Co^{2+}$ of co-factor with 10 mmol/L of L-ribulose in 50 mmole/L PIPES buffer at 70° C. for 10 minutes (see FIGS. 23 & 24).

8-4: Analysis of Two Point Mutants of Mannose-6-Phosphate Isomerase Derived from *Geobacillus thermodenitrificans* Strain Among the highest activity-residues obtained by screening the mannose-6-phosphate isomerase derived from *Geobacillus thermodenitrificans* strain, two highest activity-residues were subjected to double mutation at a time and then the activities were compared.

Figure 25:
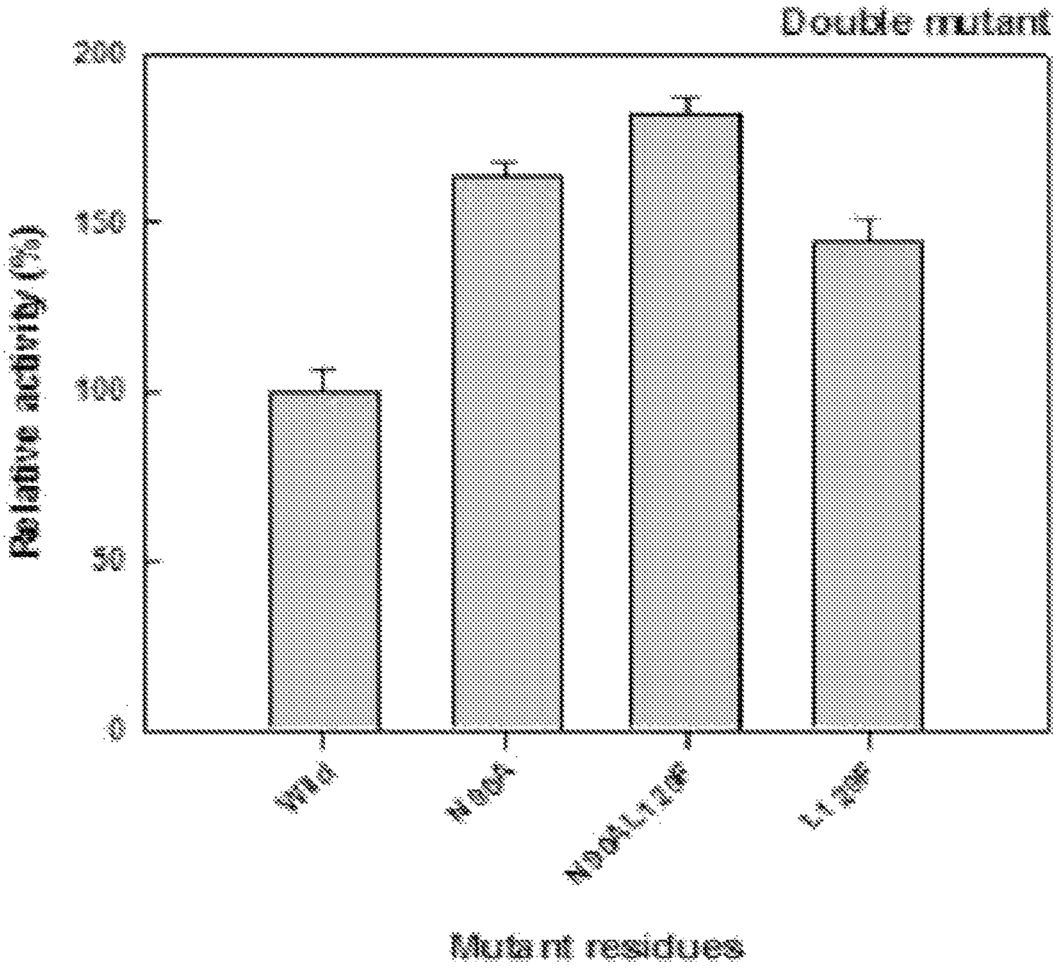
FIG. 25 is a relative activity of single mutant and double mutant enzymes at amino acid residue at positions 90 and 129 of mannose-6-phosphate isomerase enzyme according to the present invention as compared to the wide type.

Specifically, it has been seen that the activity was much higher after performing the double mutation of N90A and L129F together (see FIG. 25).

Example 9

Comparison of Conversion From L-Libulose to L-Ribose Using Mannose-6-Phosphate Isomerase and Mutant Enzyme In order to develop a method of producing ribose using the mannose-6-phosphate isomerase and mutant enzyme, the output of producing Ribose by the hour was measured using 10 mM ribulose at 65° C. of the temperature considering the time required until the enzyme activity was down by half and pH 7.0 that was the optimum pH of enzyme confirmed as mentioned above.

Figures 7, 8:
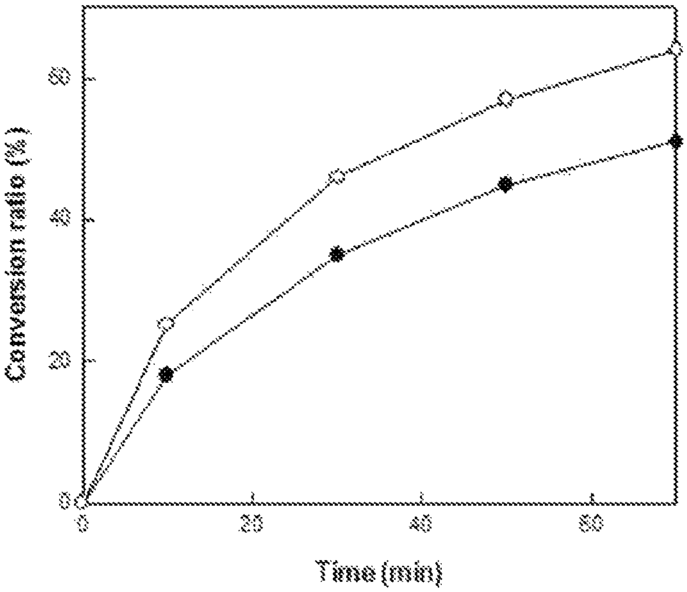
FIG. 7 is a conversion ratio of ribose by mannose-6-phosphate isomerase derived from *Thermus thermophilus* strain according to the present invention and mutant enzyme thereof (closed circle) at 10 mM of substrate concentration.
FIG. 8 is a genetic sequence of mannose-6-phosphate isomerase derived from *Thermus thermophiles* strain as set forth in SEQ ID NO: 3 according to the present invention.
Figure 11:
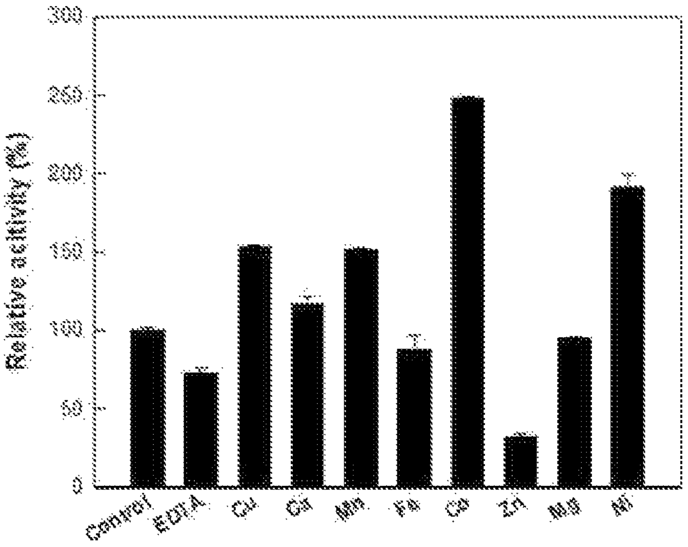
FIG. 11 is a result of comparing enzyme activities depending on a type of inorganic salt of mannose-6-phosphate isomerase derived from *Geobacillus thermodenitrificans* strain according to the present invention.
Figure 12:
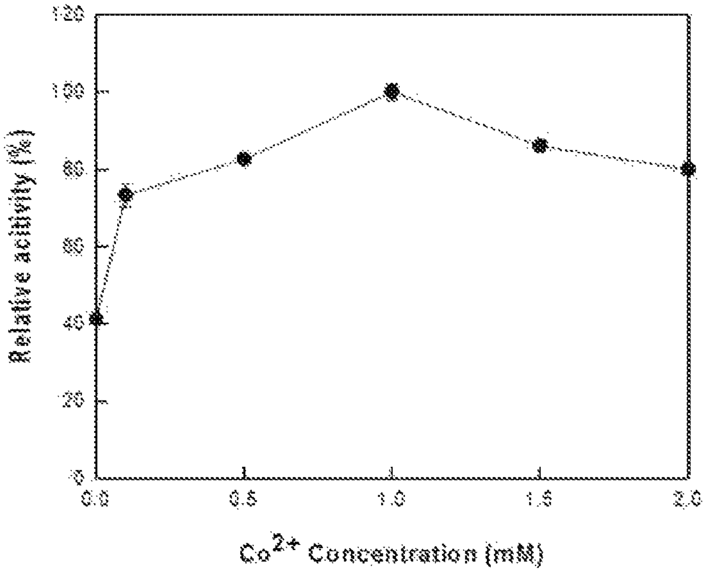
FIG. 12 is a result of comparing enzyme activities depending on the optimum concentration of inorganic salt of mannose-6-phosphate isomerase derived from *Geobacillus thermodenitrificans* stain according to the present invention.

As a result, it has been seen that the conversion rate from 10 mM ribulose to ribose after 70 minutes of the reaction was 51% for the wild enzyme and 64% for R142N mutant enzyme (see FIG. 7). From the above result, it has been seen that the mannose-6-phosphate isomerase derived from *Thermus thermophilus* exhibited the highest productivity of ribose up to now, but the mutant enzyme thereof, i.e., R142N mutant enzyme exhibited much more higher activity than it. This means that R142N mutant enzyme is the enzyme for producing L-ribose that is superior to the mannose-6-phosphate isomerase derived *Thermus thermophilus* having the highest productivity in producing biological L-ribose reported.

As set forth above, according to exemplary embodiments of the invention, the present invention can provide mannose-6-phosphate isomerase or mutant thereof, recombinant expression vectors including relevant genes, transformed microorganisms using the same, a method of producing mannose-6-phosphate isomerase in bulk using the same, and a high yield method of producing L-ribose using the mannose-6-phosphate isomerase.

The mannose-6-phosphate isomerase according to the present invention can produce ribose that is a raw material for drugs using high specificity and eco-friendly method with high yield, and the resulting L-ribose can be very useful as a starting material for the synthesis of various L-type nucleotide sugar drugs.

While the present invention has been shown and described in connection with the exemplary embodiments, it will be apparent to those skilled in the art that modifications and variations can be made without departing from the spirit and scope of the invention as defined by the appended claims.

What is claimed is:

1. A mannose-6-phosphate isomerase mutant enzyme, comprising at least one selected from the group consisting of:

a) the mutant, in which the amino acid residue Arg (R), at position 142 in the mannose-6-phosphate isomerase having SEQ ID NO: 1 is replaced with to Asn (N);

b) the mutant, in which the amino acid residues Lys (K), Ash (N), and Met (M), at positions 21, 74, and 134 in the mannose-6-phosphate isomerase as set forth in SEQ ID NO: 2 are replaced with Glu (E), Thr (T), and Arg (R), respectively;

c) the mutant, in which the amino acid residues Glu (E) and Thr (T), at positions 67 and 238 in the mannose-6-phosphate isomerase as set forth in SEQ ID NO: 2 are replaced with Gly (G) and Ile (I), respectively;

d) the mutant, in which the amino acid residue Lys (K), at position 124 in the mannose-6-phosphate isomerase as set forth in SEQ ID NO: 2 is replaced with Arg (R);

e) the mutant, in which the amino acid residue Leu (L), at position 129 in the mannose-6-phosphate isomerase as set forth in SEQ ID NO: 2 is replaced with Phe (F) or Tyr (Y);

f) the mutant of the mannose-6-phosphate isomerase selected from the group consisting of the mutants, in which the amino acid residue Asn (N), at position 90 in the mannose-6-phosphate isomerase as set forth in SEQ ID NO: 2 is replaced with Ala (A), Asp (D), His (H) or Leu (L); and g) the mutant, in which at least two residues are mutated in SEQ ID NO: 2 wherein at least one mutation is selected from those recited in the above b) to f).

2. The mannose-6-phosphate isomerase mutant enzyme of claim 1, wherein Asn (N) is replaced with Ala (A) at position 90 and Leu (L) is replaced with Phe (F) at position 129 of the mannose-6-phosphate isomerase as set forth in SEQ ID NO: 2.

* * * * *